(12) United States Patent
Panetta et al.

(10) Patent No.: US 12,408,893 B2
(45) Date of Patent: Sep. 9, 2025

(54) INTRACARDIAC DELIVERY CATHETER AND METHOD OF USE

(71) Applicant: LCMedical LLC, Minneapolis, MN (US)

(72) Inventors: Carmelo J. Panetta, Minneapolis, MN (US); Philip J. Haarstad, Chanhassan, MN (US)

(73) Assignee: TargetCath, Inc., Minneapolis, MN (US)

( * ) Notice: Subject to any disclaimer, the term of this patent is extended or adjusted under 35 U.S.C. 154(b) by 438 days.

(21) Appl. No.: 17/618,338

(22) PCT Filed: Jun. 13, 2020

(86) PCT No.: PCT/US2020/037642
§ 371 (c)(1),
(2) Date: Dec. 10, 2021

(87) PCT Pub. No.: WO2020/252416
PCT Pub. Date: Dec. 17, 2020

(65) Prior Publication Data
US 2022/0151589 A1   May 19, 2022

Related U.S. Application Data

(60) Provisional application No. 63/007,792, filed on Apr. 9, 2020, provisional application No. 62/861,906, filed on Jun. 14, 2019.

(51) Int. Cl.
*A61B 8/00* (2006.01)
*A61B 8/08* (2006.01)
(Continued)

(52) U.S. Cl.
CPC ............ *A61B 8/445* (2013.01); *A61B 8/0883* (2013.01); *A61B 8/12* (2013.01); *A61M 25/09041* (2013.01); *A61M 25/1002* (2013.01)

(58) Field of Classification Search
CPC ......... A61B 8/445; A61B 8/0883; A61B 8/12; A61M 25/09041; A61M 25/1002
See application file for complete search history.

(56) References Cited

U.S. PATENT DOCUMENTS 3,734,100 A   5/1973   Walker et al.
3,995,623 A   12/1976  Blake et al.
(Continued)

OTHER PUBLICATIONS

EPO, Partial European Search Report and Provisional Opinion for EP 20823470.8, Jun. 21, 2023 (7 pages).
(Continued)

*Primary Examiner* — Baisakhi Roy
(74) *Attorney, Agent, or Firm* — DMK Intellectual Property Law, PLLC

(57) ABSTRACT

An intracardiac delivery catheter or assembly is disclosed. The delivery catheter includes a delivery lumen and a flow assist balloon inflatable through an inflation lumen. In illustrated embodiments the delivery lumen has a diameter dimension of at least 8 F, 9 F, 10 F or between 8-14 F for insertion of an intracardiac echocardiography catheter (ICE) for placement at an intracardiac imaging site. In embodiments described, the delivery catheter is used for placement of an ICE catheter in a pulmonary artery or other treatment site using an asymmetric balloon having an asymmetric profile and portion to steer the delivery catheter, for example, into the right ventricle and into the pulmonary artery.

4 Claims, 26 Drawing Sheets

(51) Int. Cl.
   *A61B 8/12*  (2006.01)
   *A61M 25/09* (2006.01)
   *A61M 25/10* (2013.01)

(56) References Cited

U.S. PATENT DOCUMENTS

| | | | |
|---|---|---|---|
| 4,913,642 A | 4/1990 | Weber et al. | |
| 5,102,416 A | 4/1992 | Rock | |
| 5,308,317 A | 5/1994 | Ferguson et al. | |
| 5,383,853 A | 1/1995 | Jung et al. | |
| 5,387,226 A | 2/1995 | Miraki | |
| 5,571,161 A | 11/1996 | Starksen | |
| 5,879,499 A | 3/1999 | Corvi | |
| 6,129,737 A | 10/2000 | Hamilton et al. | |
| 6,379,372 B1 | 4/2002 | Dehdashtian et al. | |
| 6,491,671 B1 | 12/2002 | Larson, III et al. | |
| 6,966,902 B2 | 11/2005 | Tsugita et al. | |
| 8,409,103 B2 | 4/2013 | Grunwald et al. | |
| 8,932,223 B2 | 1/2015 | Emelianov et al. | |
| 9,204,819 B2 | 12/2015 | Grunwald et al. | |
| 9,492,658 B2 | 11/2016 | Shireman et al. | |
| 10,368,837 B2 | 8/2019 | Grunwald et al. | |
| 2001/0023332 A1 | 9/2001 | Hahnen | |
| 2003/0028097 A1 | 2/2003 | D'Amico et al. | |
| 2004/0049158 A1 | 3/2004 | Ley et al. | |
| 2005/0020914 A1* | 1/2005 | Amundson | A61B 8/12 600/431 |
| 2005/0159645 A1 | 7/2005 | Bertolero et al. | |
| 2007/0038239 A1 | 2/2007 | Ritchie | |
| 2007/0293754 A1 | 12/2007 | Schneid et al. | |
| 2008/0097402 A1 | 4/2008 | Hoganson et al. | |
| 2009/0118612 A1* | 5/2009 | Grunwald | A61B 8/42 600/453 |
| 2010/0152590 A1* | 6/2010 | Moore | A61B 8/4461 600/466 |
| 2011/0021911 A1 | 1/2011 | Waters et al. | |
| 2011/0098561 A1 | 4/2011 | Thornton et al. | |
| 2012/0221071 A1* | 8/2012 | Karlsson | A61N 1/3627 607/18 |
| 2012/0221092 A1* | 8/2012 | Jaffe | A61B 17/12136 604/533 |
| 2013/0238045 A1* | 9/2013 | Blomqvist | A61N 1/365 607/18 |
| 2017/0035987 A1* | 2/2017 | Ardehali | A61M 1/3666 |
| 2018/0064415 A1* | 3/2018 | Zhai | A61N 7/02 |
| 2019/0357876 A1* | 11/2019 | Grunwald | A61B 90/11 |
| 2020/0238107 A1* | 7/2020 | Shabtay | A61K 31/506 |
| 2020/0269059 A1* | 8/2020 | Kaiser | A61N 1/37205 |
| 2021/0000479 A1* | 1/2021 | Rabin | A61B 17/1285 |
| 2022/0054138 A1* | 2/2022 | Rabin | A61B 17/12136 |

OTHER PUBLICATIONS

ISA/US International Search Report for PCT/2020/37642, Sep. 10, 2020, 2 pages.

ISA/US International Written Opinion for PCT/2020/37642, Sep. 10, 2020, 5 pages.

* cited by examiner

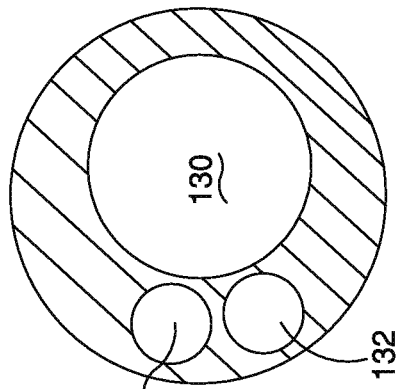
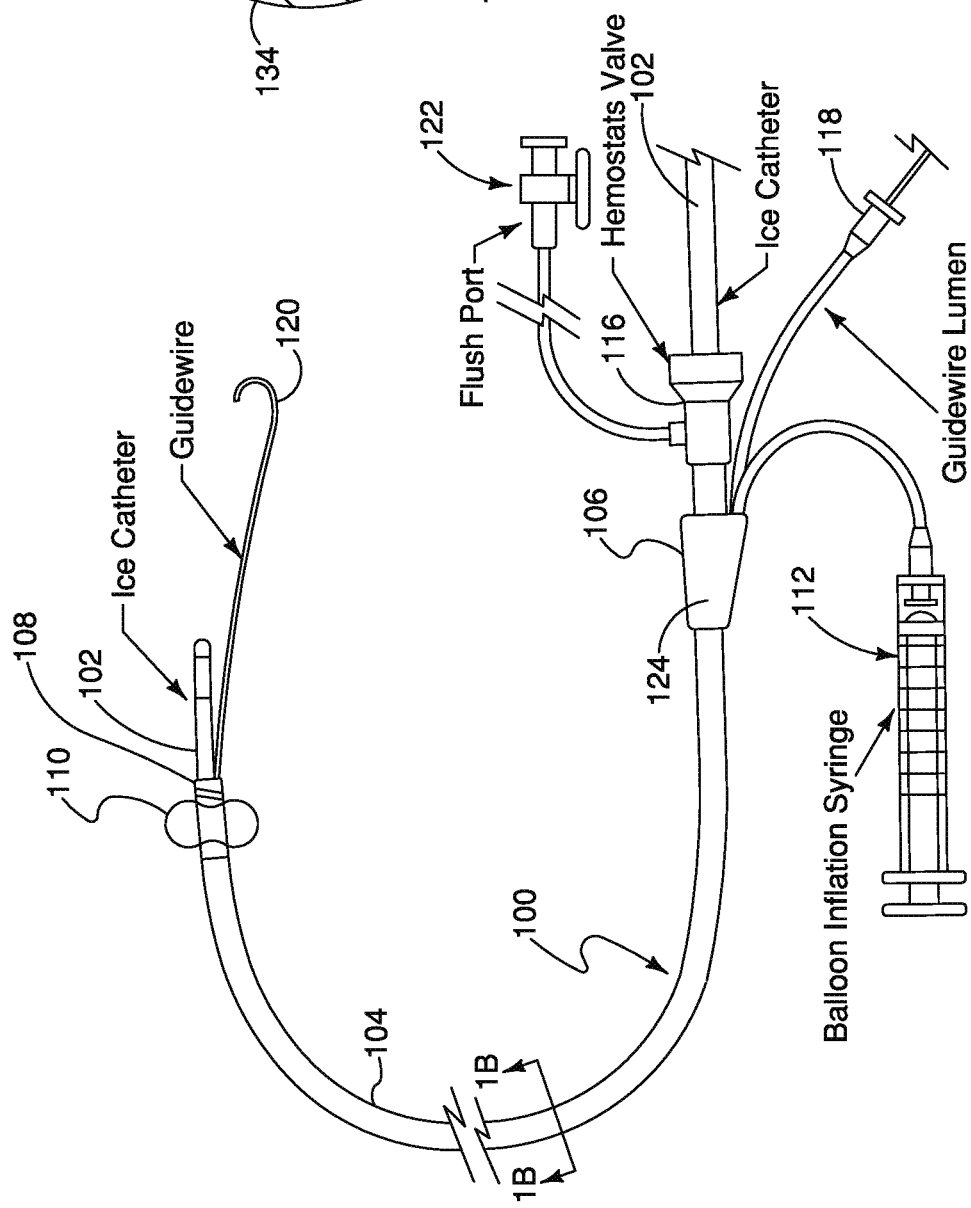
FIG.1B
FIG.1A

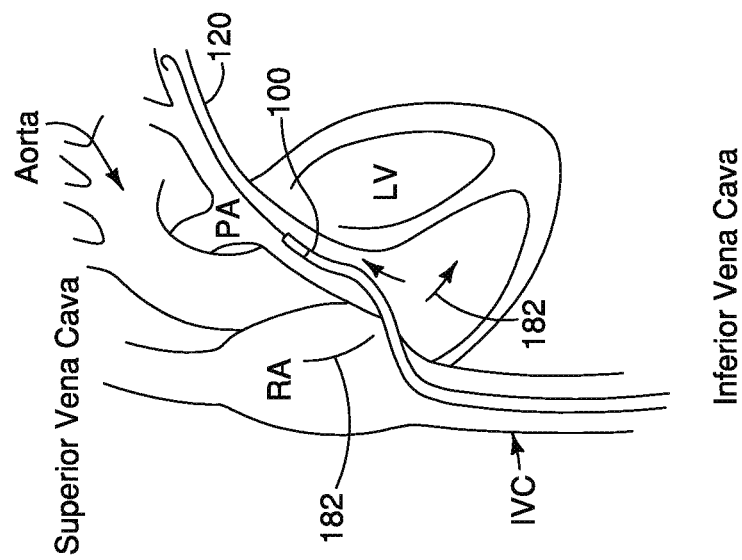
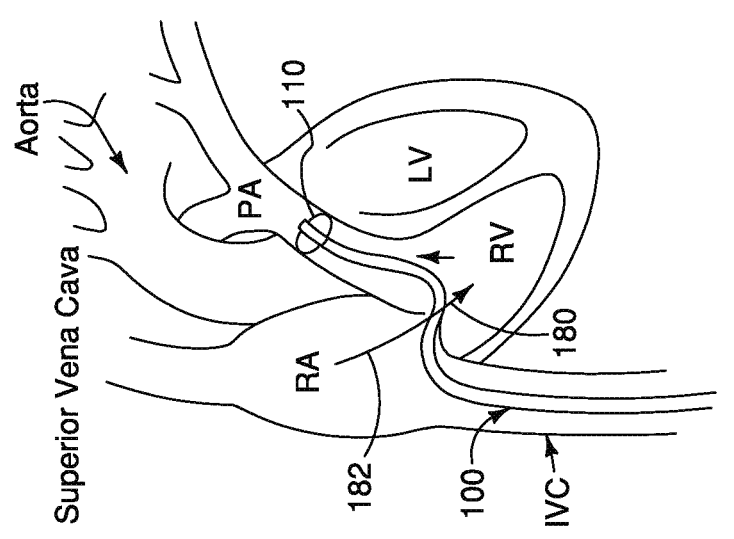
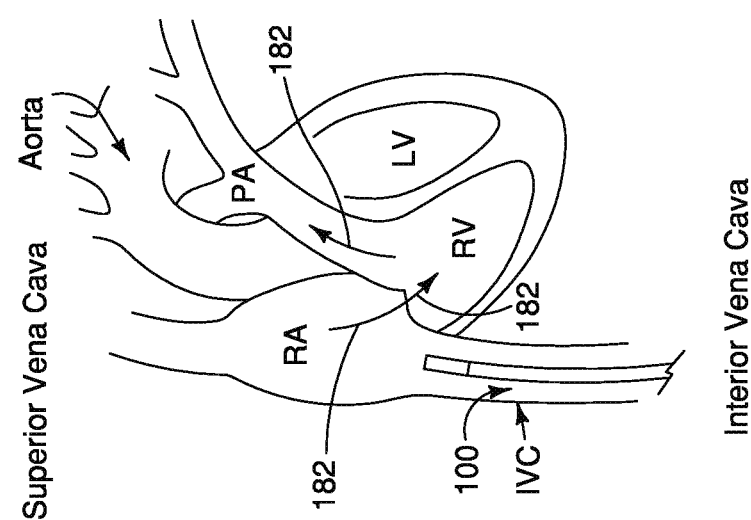
FIG. 2C
FIG. 2B
FIG. 2A

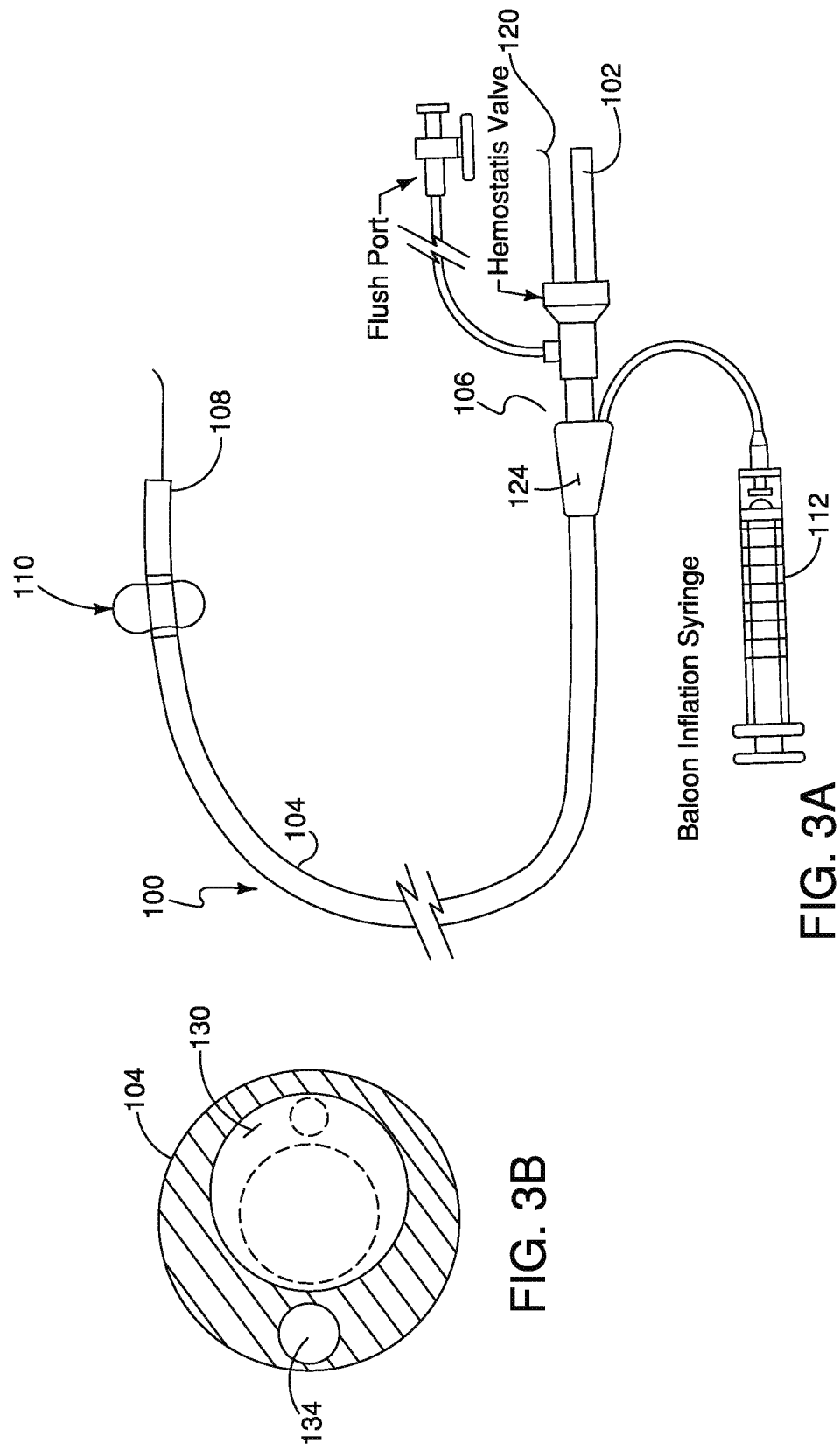

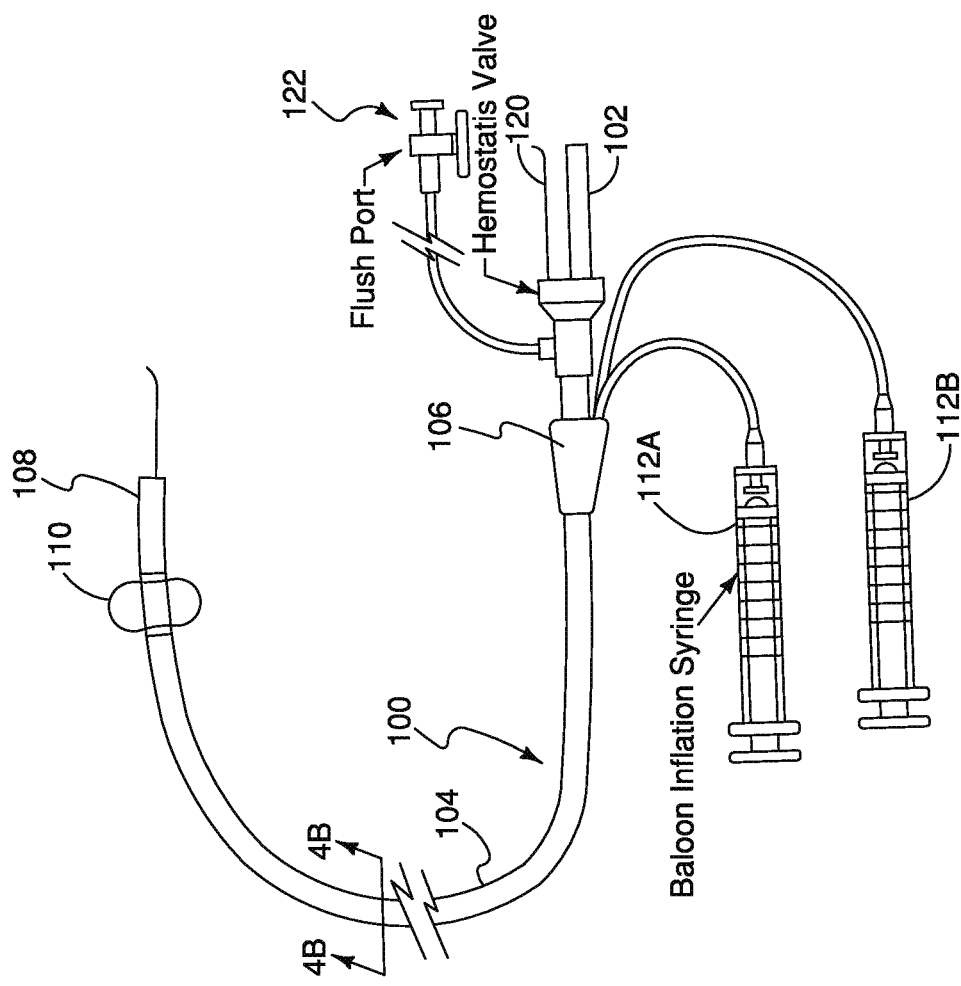
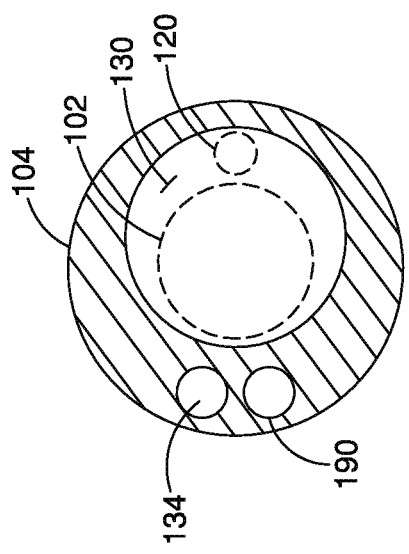
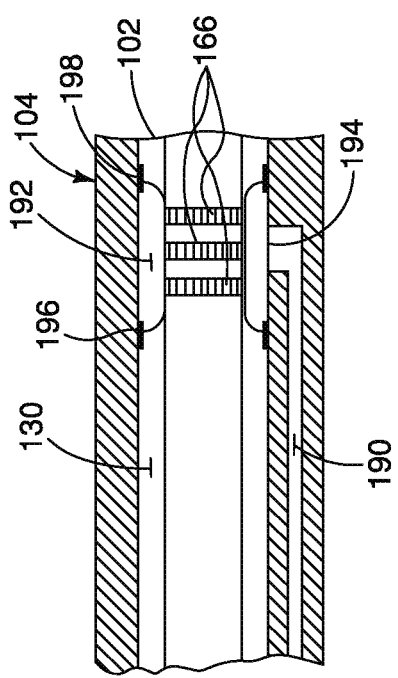
FIG. 4A
FIG. 4B
FIG. 4C

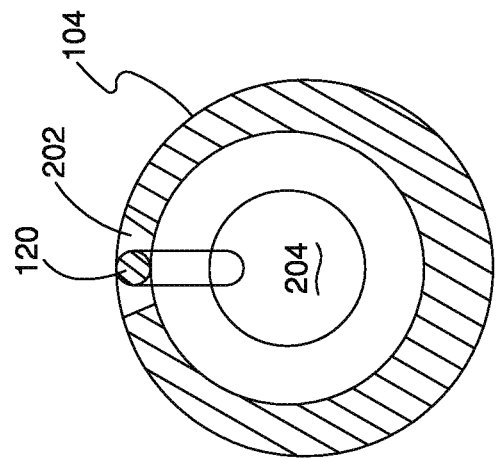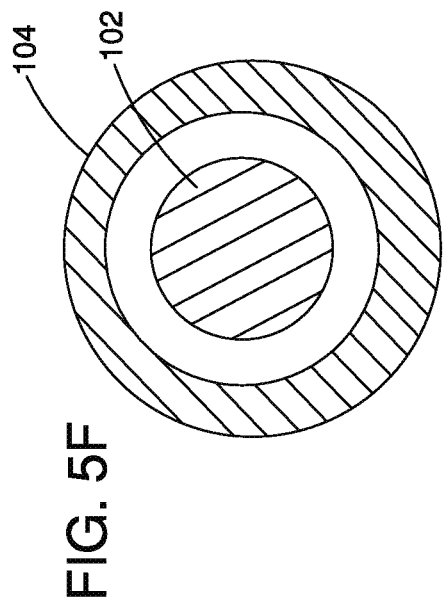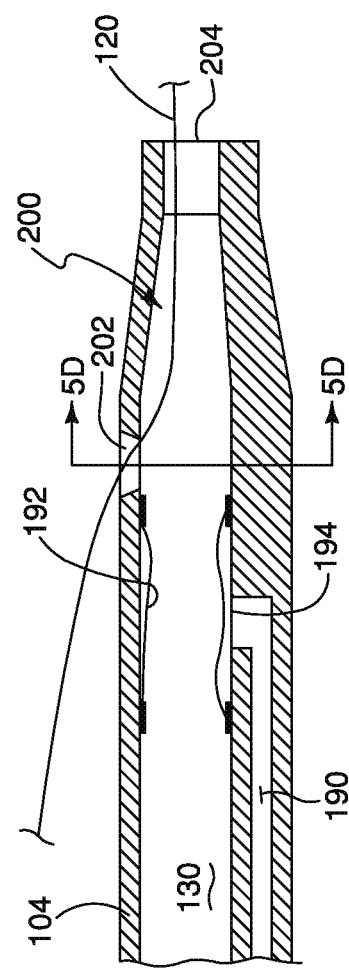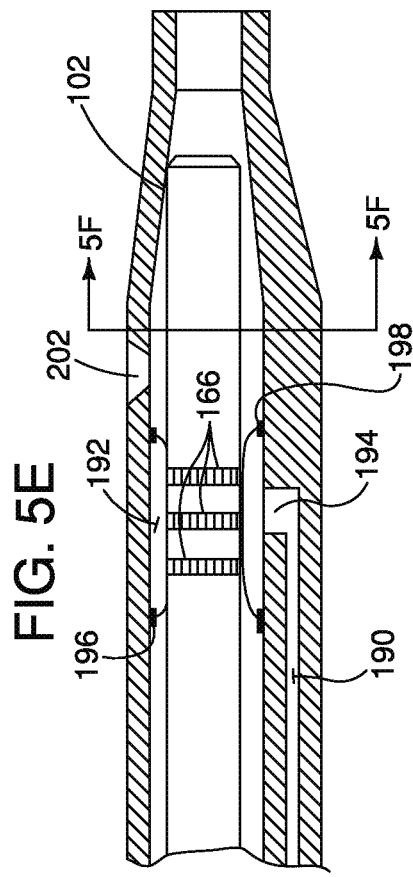

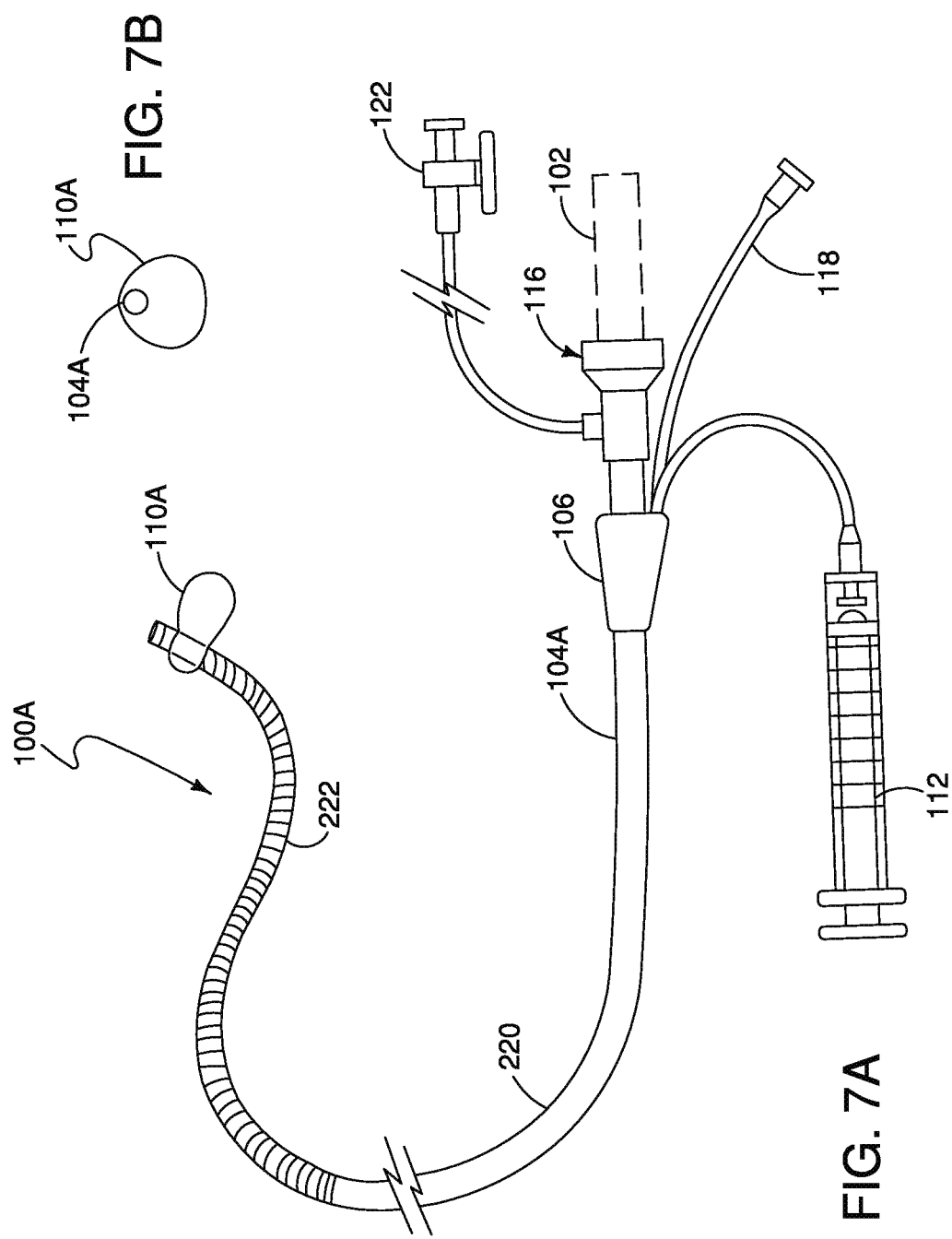

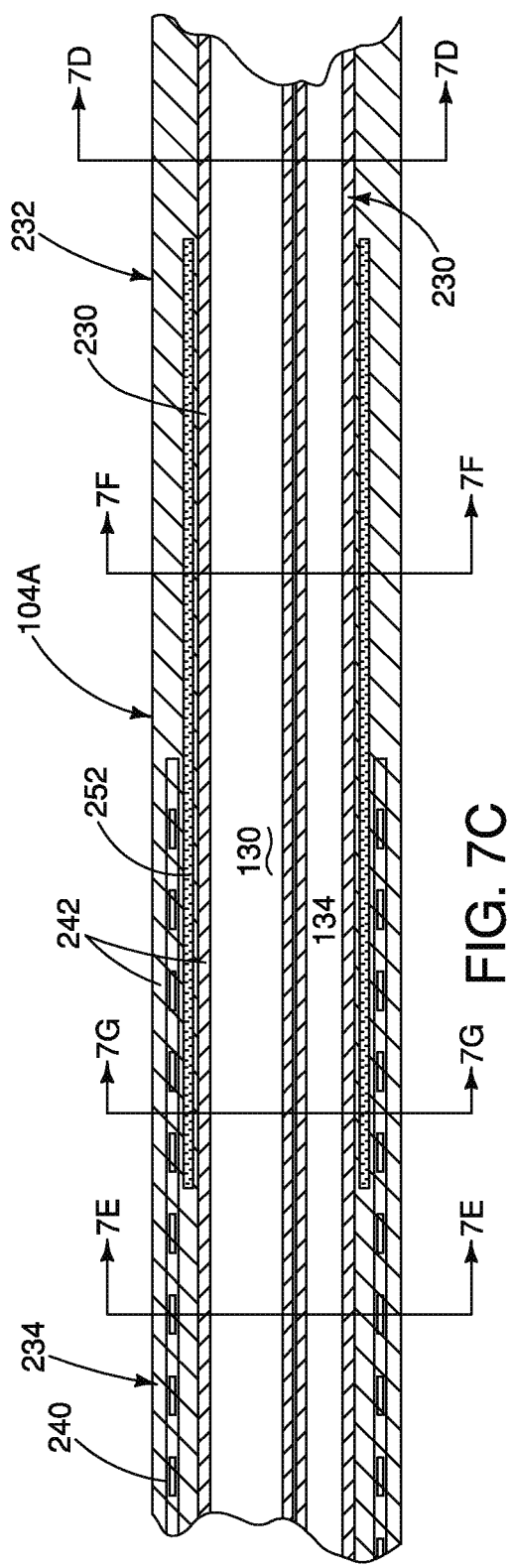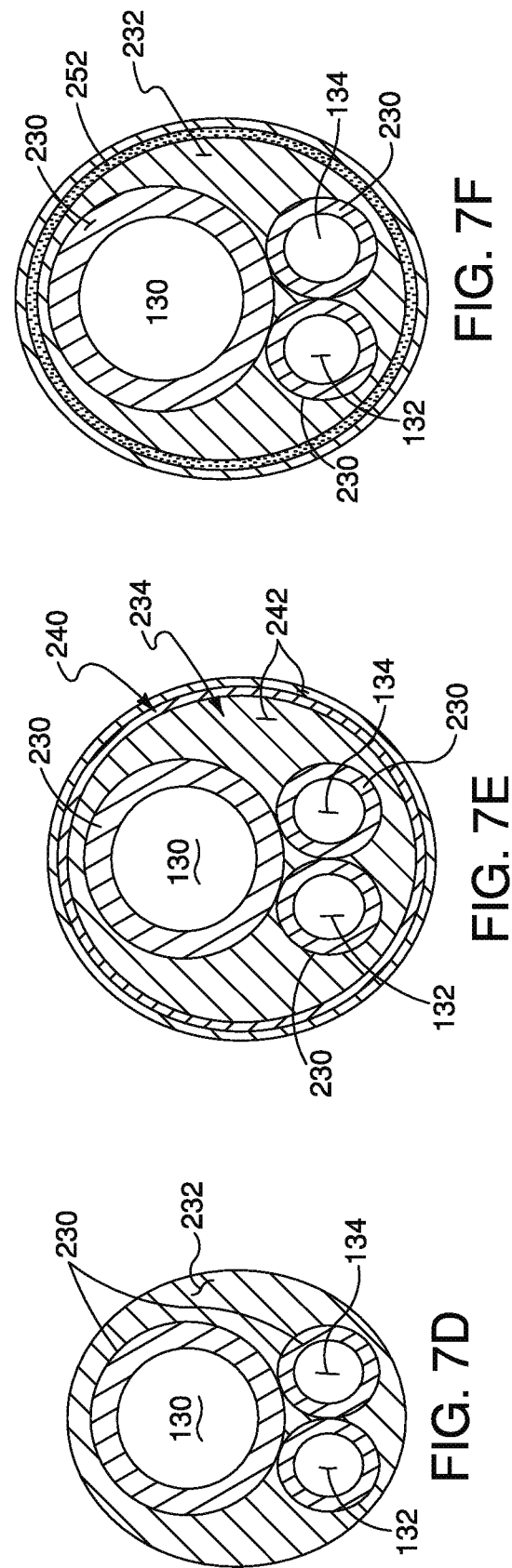
FIG. 7C
FIG. 7D
FIG. 7E
FIG. 7F

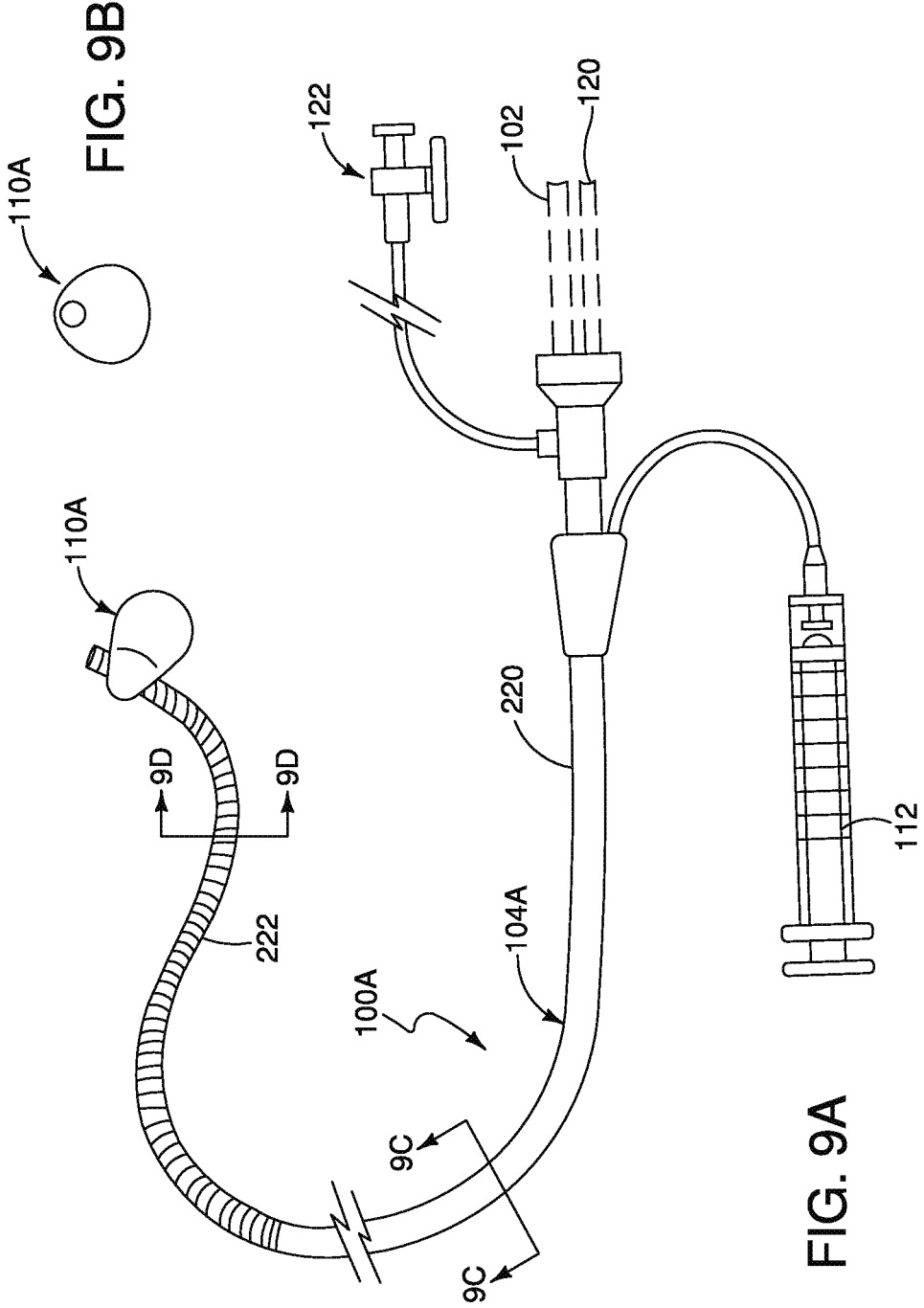
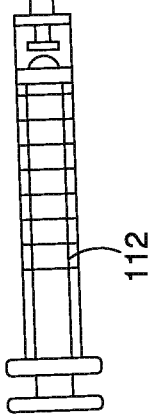
FIG. 9B
FIG. 9A

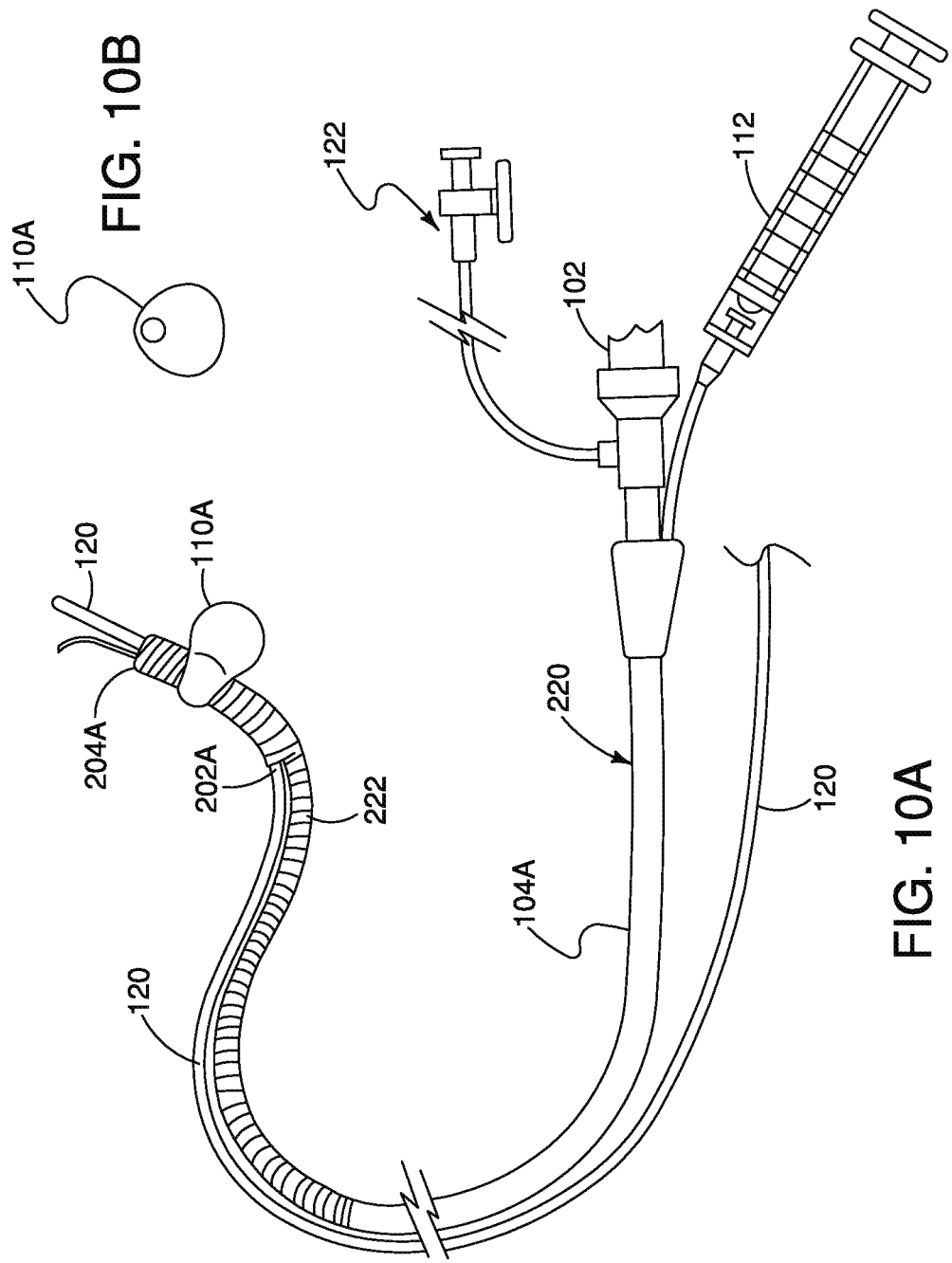

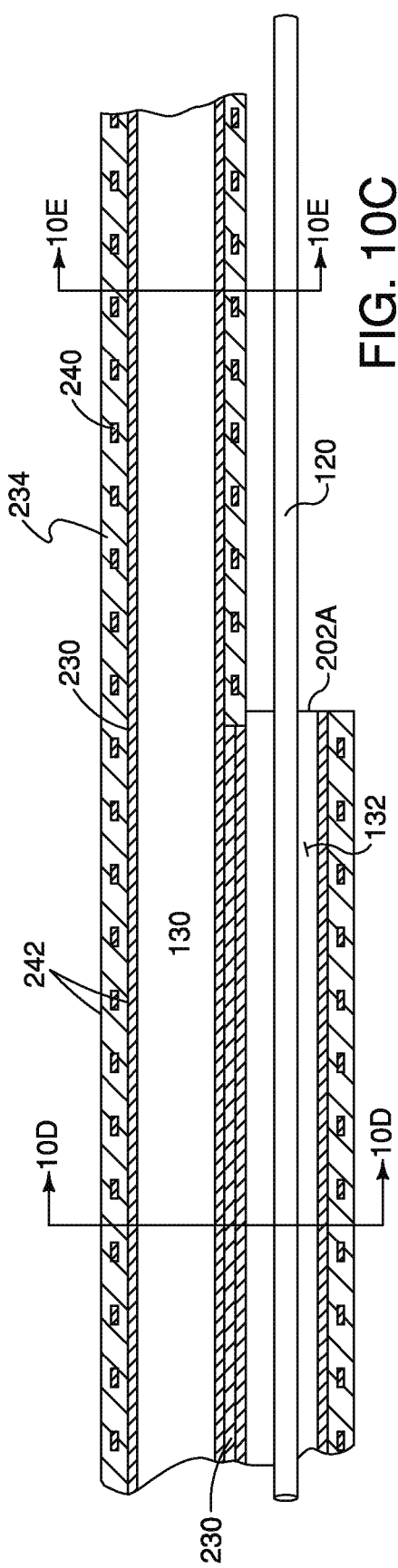
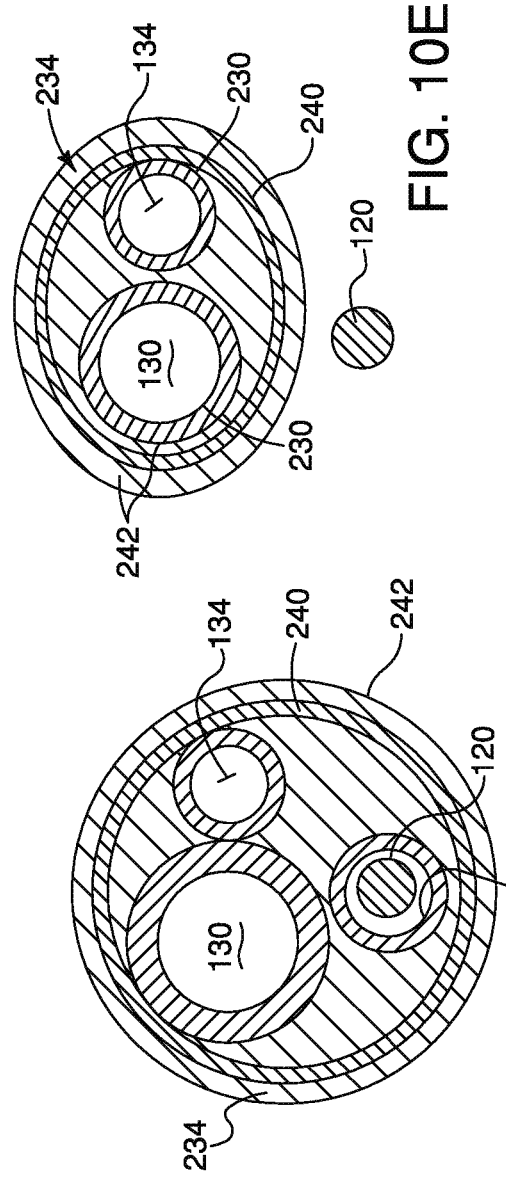
FIG. 10C
FIG. 10E
FIG. 10D

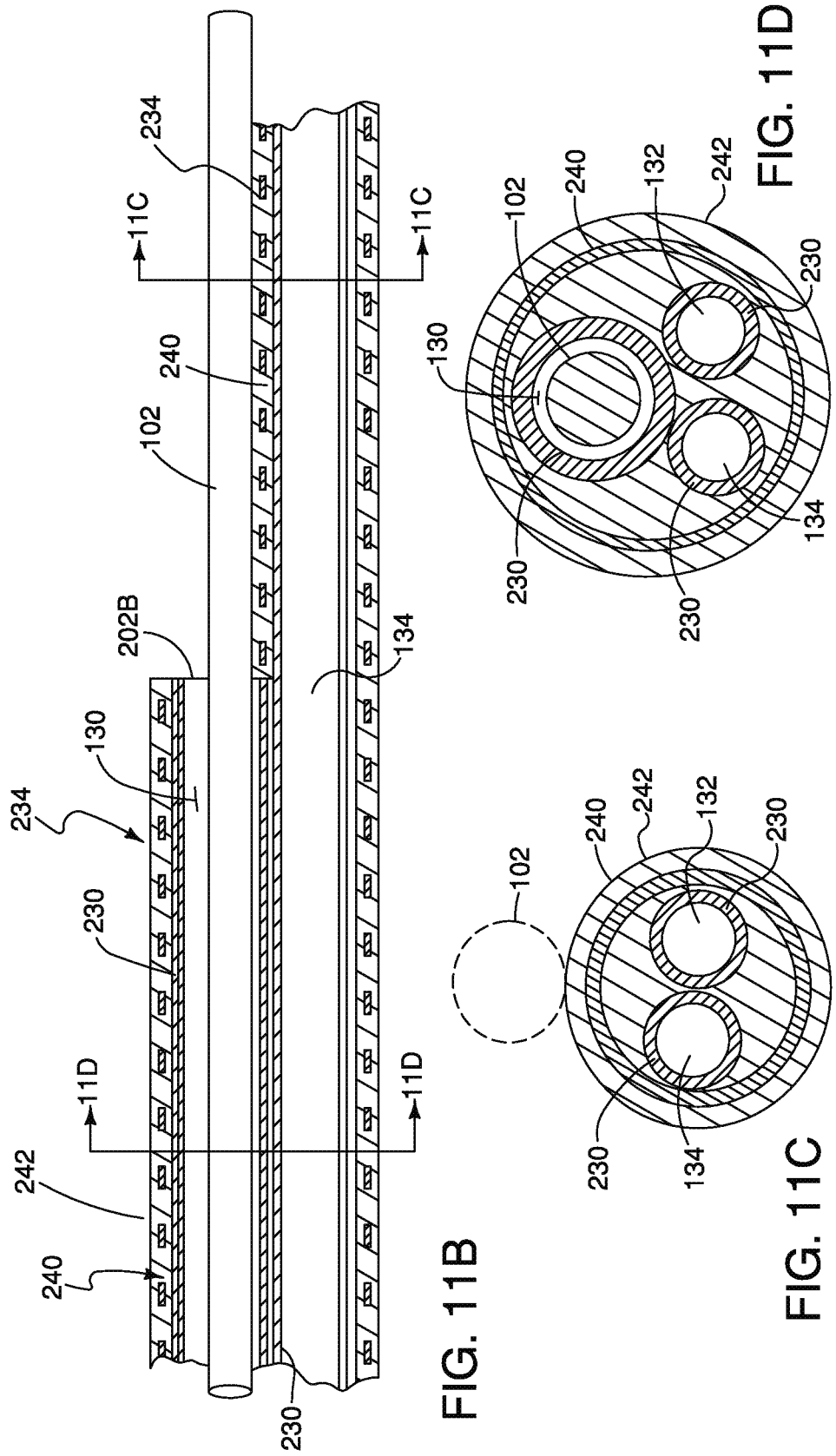

INTRACARDIAC DELIVERY CATHETER AND METHOD OF USE

CROSS-REFERENCE TO RELATED APPLICATION

The present application claims priority to U.S. Ser. No. 62/861,906 filed Jun. 14, 2019 and entitled INTRACARDIAC IMAGING ASSEMBLY AND METHOD OF USE and U.S. Ser. 63/007,792 filed Apr. 9, 2020 entitled INTRACARDIAC DELIVERY CATHETER AND METHOD OF USE, the content of which are hereby incorporated in the present application in their entirety.

BACKGROUND

Various cardiac treatment procedures require use of an imaging device during the treatment procedure. Intracardiac placement of the imaging or other therapeutic device into the pulmonary artery or other intracardiac treatment site can be difficult and during use, the device can prolapse making the treatment procedure more difficult and cumbersome.

SUMMARY

The present application relates to an intracardiac delivery catheter for intracardiac placement of an imaging or treatment device for use. In the illustrated embodiments, the delivery catheter includes a flow assist balloon for intracardiac placement of the delivery catheter and a delivery lumen therethrough. In illustrated embodiments, the delivery lumen has a diameter dimension of at 8 F, 9 F or 10 F for insertion of an intracardiac echocardiography catheter or intracardiac echocardiography (ICE) catheter and guidewire. For example, in embodiments disclosed, the delivery lumen has a diameter dimension between 8 F-14 F or 9 F-14 F. The delivery lumen extends from an inlet at the proximal end of a catheter shaft to a distal end of the catheter shaft. In illustrated embodiments an outlet of the delivery lumen is distal from a flow assist balloon of the delivery catheter and is formed through an opened distal end of the catheter shaft and delivery lumen. Embodiments of the delivery catheter include a guide wire lumen in addition to the delivery lumen and an inflation lumen to expand the flow assist balloon for intracardiac placement of the delivery catheter. In an illustrated embodiment, the guide wire lumen is a shortened guide wire lumen.

Embodiments of the intracardiac delivery catheter include an asymmetric shaped flow assist balloon having an asymmetric shape in an inflated or expanded profile. As disclosed the asymmetric shape provides a moment arm or asymmetric portion relative to a longitudinal axis of the catheter shaft to steer the catheter shaft around acute angles, for example though the tricuspid and pulmonary valves for placement in a pulmonary artery. As disclosed, in illustrated embodiments, the delivery lumen is used for intracardiac delivery of materials, imaging catheters or other treatment devices.

Embodiments of the multiple lumen delivery catheter include an inner balloon in the delivery lumen to engage an imaging or echocardiography catheter inserted in the delivery lumen. As disclosed, in illustrated embodiments the length of the delivery catheter is sized for intracardiac placement in a pulmonary artery or other intracardiac site. The delivery catheter can be inserted through a femoral vein into the right atrium through the inferior vena cava or through the superior vena cava via a jugular vein. In illustrated embodiments, the elongate length of the catheter shaft has a varied stiffness or flexibility including a relatively flexible distal portion.

The present application provides a kit for intracardiac imaging including a multiple lumen delivery catheter and intracardiac echocardiography catheter for cardiac imaging and treatment. In illustrated embodiments, the multiple lumens include a delivery lumen, a guide wire lumen and an inflation lumen to inflate a flow assist balloon. In embodiments disclosed the delivery lumen has a diameter of at least 8 F, 9 F or 10 F or between 8 F-14 F or 9 F-14 F for insertion of the intracardiac echocardiography catheter. For use, the delivery catheter is inserted into a right atrium, right ventricle for placement into a pulmonary artery. The delivery catheter is tracked to the right atrium through the inferior vena cava or superior vena cava.

In alternate embodiments, the delivery catheter is used for placement of an imaging catheter in the superior vena cava, pulmonary artery or alternate intracardiac imaging site. In illustrated embodiments, the catheter shaft includes a guidewire lumen for intracardiac placement, a flow assist balloon and a delivery lumen sized for insertion of an intracardiac echocardiography catheter. In another embodiment, the delivery catheter includes a flow assist balloon and a delivery lumen having a smaller dimension for medication or other treatment or imaging devices or asymmetric balloon and delivery lumen. Details of the present invention are described in the following drawings and description.

BRIEF DESCRIPTION OF DRAWINGS

FIG. 1A illustrates an embodiment of an assembly of the present application.

FIG. 1B is a cross-sectional view as taken along line 1B-1B of FIG. 1A of the flow assisted delivery catheter shown without a guidewire and imaging catheter inserted.

FIGS. 2A-2E progressively illustrate a process for using the assembly of the present application for intracardiac imaging.

FIGS. 3A-3B illustrate another embodiment of the assembly of the present application.

FIG. 4A illustrates another embodiment of the assembly of the present application.

FIG. 4B is a cross-sectional view as taken along line 4B-4B of FIG. 4A.

FIG. 4C is a cross-sectional view of a portion of the delivery catheter shown with the imaging catheter in the delivery lumen and an inner balloon inflated.

FIG. 5C is a sectional view of the distal end of the delivery catheter shown with a guidewire extending through a guidewire lumen formed along a distal end of the delivery lumen.

FIG. 5D is a cross-sectional view as taken along line 5D-5D of FIG. 5C.

FIG. 5E is a sectional view of the delivery catheter having an ICE catheter inserted into the delivery lumen and the inner balloon inflated to abut the ICE catheter.

FIG. 5F is a cross-sectional view as taken along line 5F-5F of FIG. 5E.

FIG. 7A illustrates another embodiment of an intracardiac delivery catheter of the present application.

FIG. 7B illustrates an end view of a flow assist balloon of an embodiment of the intracardiac delivery catheter.

FIG. 7C is a longitudinal cross-sectional view of the intracardiac delivery catheter of FIG. 7A including a stiff proximal length and a relatively flexible distal length.

FIG. 7D is a cross-sectional view taken along line D-D of FIG. 7C.

FIG. 7E is a cross-sectional view taken along line E-E of FIG. 7C.

FIG. 7F is a cross-sectional view taken along line F-F of FIG. 7C.

FIG. 9A schematically illustrates another embodiment of an intracardiac delivery catheter of the present application.

FIG. 9B illustrates an end view of an asymmetric flow assist balloon.

FIG. 10A illustrates another embodiment of an intracardiac delivery catheter of the present application having a shortened guide wire lumen.

FIG. 10B is an end view of a flow assist balloon of the intracardiac delivery catheter of FIG. 10A.

FIG. 10C is a cross-sectional view of the delivery catheter of FIG. 10A illustrating a shortened guide wire lumen.

FIG. 10D is a cross-sectional view taken along line D-D of FIG. 10C.

FIG. 10E is a cross-sectional view taken along line E-E of FIG. 10C.

FIG. 11B is a cross-sectional view of the delivery catheter of FIG. 11A illustrating the imaging catheter lumen.

FIG. 11C is a cross-sectional view taken along line C-C of FIG. 11B.

FIG. 11D is a cross-sectional view taken along line D-D of FIG. 11B.

In the above-referenced FIGS., like numbers are used to identify like parts. It should be noted that features in the FIGS. are not necessarily drawn to scale.

DETAILED DESCRIPTION OF ILLUSTRATIVE EMBODIMENTS

Figure 1D:
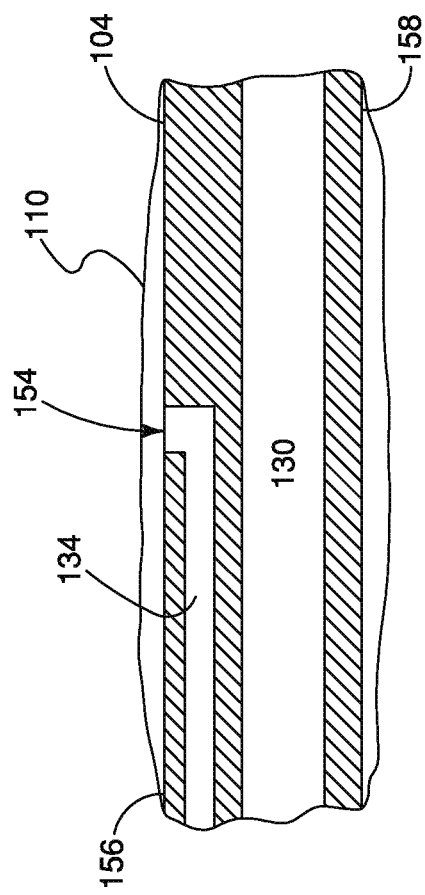
FIG. 1D is a detailed cross-sectional view of a portion of the catheter of FIG. 1A with a flow assist balloon illustrated in a deflated condition.

The present application relates to an assembly and method for intracardiac imaging. Illustrative embodiments of the assembly use an echocardiography catheter to provide an intracardiac image for medical treatment. Placement of the imaging catheter at an imaging site can be difficult due to the anatomy of the heart or desired image. Embodiments of the present application provide an assembly and method for placement of the imaging catheter in a pulmonary artery, superior vena cava or other intracardiac site to provide a feedback image for treatment.

Illustrative embodiments of the present assembly include an intracardiac delivery catheter (IDC) 100 for placement of the imaging catheter such as an intracardiac echocardiography catheter (ICE catheter) 102 for use. The intracardiac delivery catheter 100 is formed of an elongate shaft 104 having an elongate length extending between a proximal end 106 and a distal end 108. In an illustrated embodiment, the shaft 104 is formed of a flexible material having sufficient length to track from an insertion site into a pulmonary artery through a patient's right atrium and right ventricle or other treatment as will be described herein. In illustrated embodiments, the insertion site is a femoral vein or jugular vein.

The shaft 104 of the catheter 102 is bendable and has sufficient stiffness and torquability to navigate the circuitous path from the insertion site for intracardiac placement at the imaging site. The length of the catheter body 104 can have varied flexibility to navigate through a patient's body to the intracardiac treatment site. In an illustrated embodiment, the approximate length of the delivery catheter is between 60-90 cm, however in other embodiments, the length is between 50-120 cm. As shown the catheter 102 includes a flow assist balloon 110 coupled to the catheter shaft 104 proximate to the distal end 108. Inflation fluid is injected into the flow assist balloon 110 through an inflation syringe 112 or other inflation device coupled to the proximal end 106 of the shaft 104. The proximal end 106 of the shaft 104 also includes a hemostatic connector 116 for the ICE catheter 102 and connector 118 providing a port for a guidewire 120. In the illustrated embodiment, the hemostatic connector 116 includes a flushing port 122. As shown, sleeve 124 encloses attachment of the proximal connectors 116, 118 and syringe 112 to form a proximal hub of the delivery catheter 100.

As shown in the cross-sectional view of FIG. 1B, the shaft 104 of the flow assisted delivery catheter 100 includes a plurality of lumens along the length of the shaft 104. The plurality of lumens include an delivery lumen 130 having a diameter sized for insertion of the ICE catheter 102 therethrough, a guidewire lumen 132 and an inflation lumen 134. The delivery catheter lumen 130 has an elongate length that extends from the proximal end 106 of the shaft 104 proximate to the distal end 108. The ICE catheter 102 is inserted through the hemostatic connector 116 coupled to the proximal end of lumen 130 and is slidably advanced through the lumen 130 for use. In the illustrated embodiment, lumen 130 has an opened distal end. In an illustrated embodiment, a diameter of the delivery lumen 130 is at least 8 F, 9 F or 10 F or between 8-14 F or 9-14 F (French catheter diameter scale) to accommodate a 3D intracardiac echocardiography catheter 102.

Figure 1C:
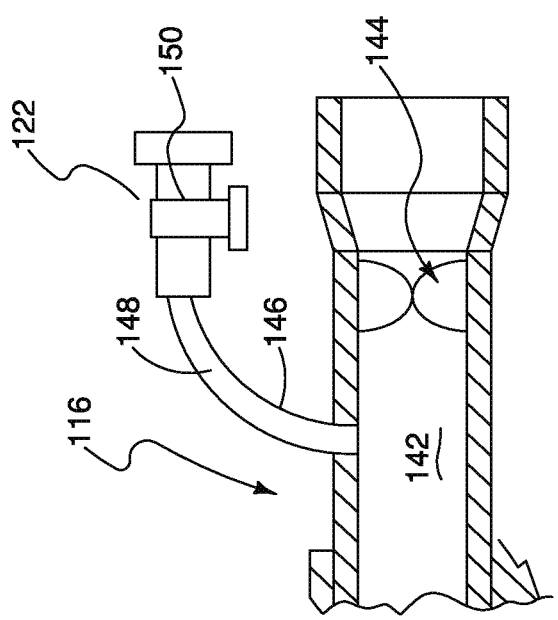
FIG. 1C illustrates a hemostatic connector coupled to a delivery lumen.

As shown in FIG. 1C, the hemostatic connector 116 is formed of a connector body 140 having a passageway 142 extending between opposed ends of the connector body 140. The connector body 140 includes a flexible hemostatic valve structure (e.g. gasket) 144 (illustrated diagrammatically) along the passageway 142. The flushing port 122 is coupled to the passageway 142 of connector 116 through a branch structure 146 having a branch passageway 148. Flow of fluid through the branch passageway 148 is controlled via a flushing port valve 150 operable between an opened position and a closed position to open and close the flushing port 122. Application is not limited to a particular hemostatic valve structure 144 and various designs can be employed as will be appreciated by those skilled in the art.

Figure 1E:
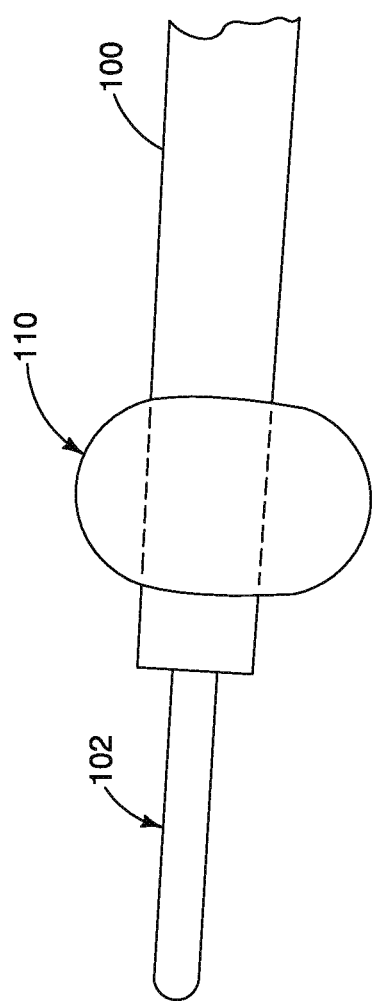
FIG. 1E is a detailed illustration of a distal end of the assembly of FIG. 1A illustrating the flow assist balloon inflated for use.

The guidewire lumen 120 has an elongate length that extends from the proximal end 106 of the catheter shaft 104 to the distal end of the catheter shaft 104. The guidewire 120 is inserted through connector 118 and slidably advanced through lumen 132 for placement through an opened distal end of the guidewire lumen 132. The inflation lumen 134 extends along the elongate shaft 104 to inject inflation fluid into the flow assist balloon 110 through an inflation port 154 connecting the inflation lumen 134 to an interior of the flow assist balloon 110 as shown in FIG. 1D. The balloon 110 is formed of an elastomeric or other balloon material having a proximal collar 156 connected about the cylindrical body 104 aft of the inflation portion 154 and a distal collar 158 connected about the cylindrical body 104 forward of the inflation port 154. Inflation fluid is injected into the lumen 134 through syringe 112 to inflate the flow assist delivery balloon 110 as shown in FIG. 1E. As will be appreciated by those skilled in the art, the balloon is a Swan-Ganz type balloon having a construction as described in U.S. Pat. No. 3,634,924, the contents of which is incorporated by reference into the present application.

Figure 1F:
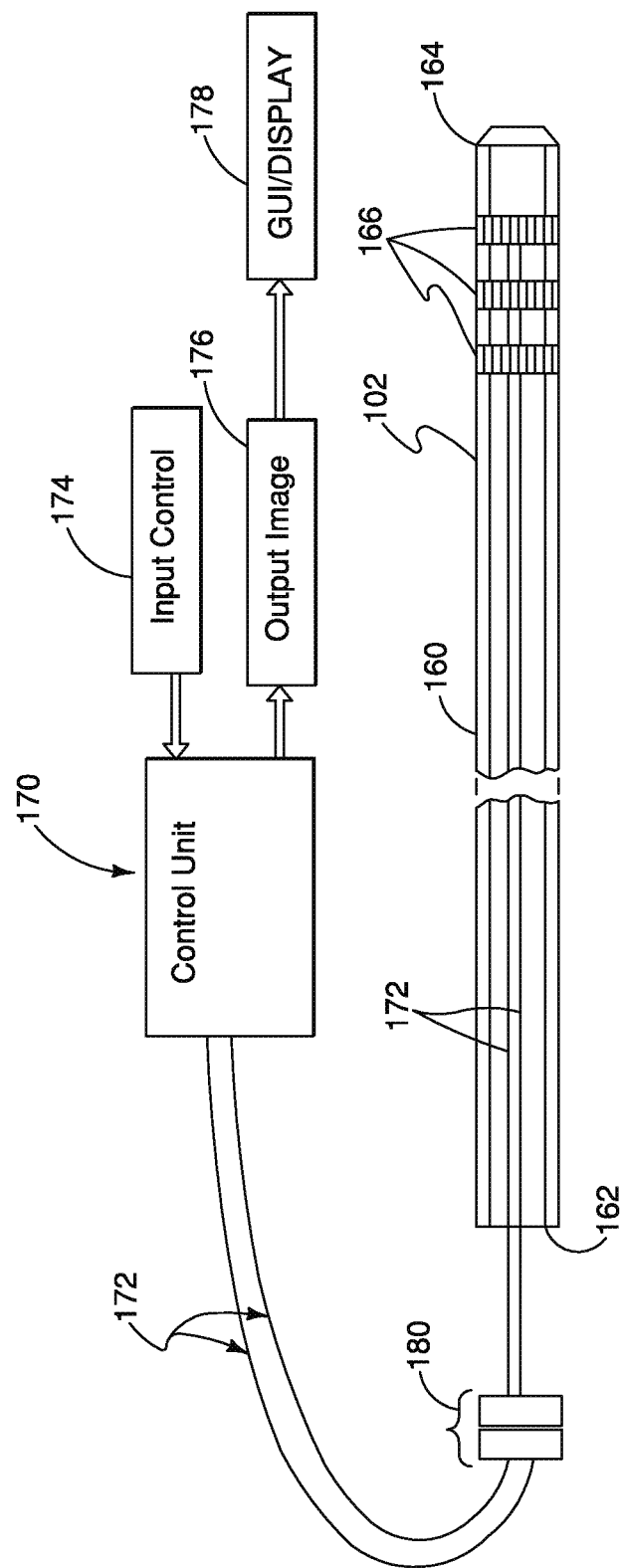
FIG. 1F schematically illustrates an embodiment of an intracardiac imaging catheter (ICE) of the present application.

As previously described, the delivery catheter 100 is configured for placement of ICE catheter 102 at an imaging site via insertion through the delivery lumen 130. Illustrative imaging catheters include 2D and 3D intracardiac echocardiography imaging catheters. FIG. 1F is an illustrative embodiment of an ICE imaging catheter 102 for placement via delivery catheter 100. As shown, the ICE catheter 102 has an elongate tubular body or shaft 160 having an elongate length extending between a proximal end 162 and a distal end 164. The elongate length of the tubular body has sufficient flexibility, steerability and length for intracardiac placement in a pulmonary artery or other intracardiac imaging site from an insertion site. A plurality of transducer elements or transducer arrays 166 (illustrated diagrammatically) are coupled to the distal end of the elongate body 160 to generate ultrasonic waves or vibration and detect feedback vibration or excitation for imaging. As shown the transducer elements 166 are coupled to a control unit 170 through a plurality of wires/leads 172 and socket connection 180 to provide an input excitation or vibration and receive feedback vibration or excitation. In an illustrated embodiment, the ICE catheter 102 includes separate transducers 166 for transmitting and receiving ultrasonic vibration or the same transducers can be used as both transmitters and receivers.

Figure 1G:
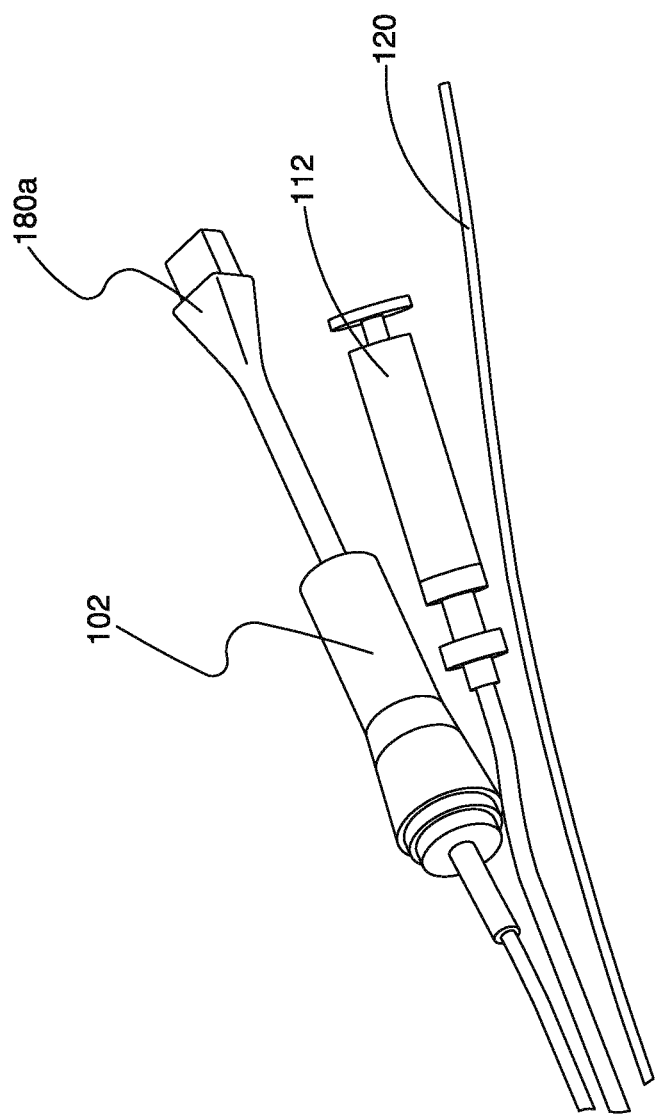
FIG. 1G illustrates a proximal end of the assembly and imaging catheter.

The control unit 170 includes circuitry to generate ultrasonic or echoing high frequency vibration in response to input control 174 and process feedback signals from the transducer elements 166 to provide an output image 176 for display on a GUI device 178. The control unit 170 is coupled to a power source for use and is coupled to the transducer elements 166 through one or more circuit elements and/or flex circuits. Illustrative transducer elements 166 include an array of piezoelectric elements, capacitive elements or other electromechanical transducer elements for generating ultrasonic vibration or disturbance and detecting feedback vibrations. In an illustrated embodiment as shown in FIGS. 1E-1F, the imaging catheter 102 has a rounded or contoured distal tip for intracardiac placement. As shown in FIG. 1G, in an illustrated embodiment, the plug and socket connection 180 includes a plug 180a connected to the distal end of the ICE catheter 102 which connects to a socket (not shown) connected to the control unit 170.

Figure 2E:
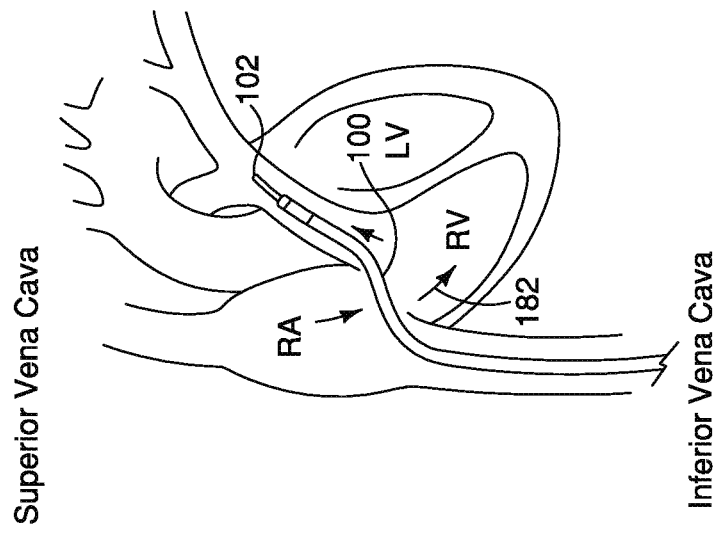

As previously described, the present delivery catheter 100 has application for intracardiac placement of the ICE catheter 102 in the heart. The heart includes a right ventricle (RV) which provides blood flow into the pulmonary artery (PA). Blood flows into the right ventricle (RV) from the right atrium (RA) and from the superior vena cava or the inferior vena cava. The pulmonary artery (PA) is near the aorta which receives blood flow from the right ventricle (RV). The position of the pulmonary artery (PA) near the aorta provides a practical site to image the aorta or other structures of the heart for both electrophysiology and structural procedures. Because of the structure of the heart, placement of the ICE catheter 102 through the right atrium (RA) into the right ventricle (RV) and pulmonary artery (PA) is difficult. In particular, in order to position the imaging catheter 102 into the pulmonary artery (PA) from the right ventricle (RV) the catheter must be guided and steered along an "S" curve path and often can fall back into the right ventricle due to the tortuous path. Use of the present assembly facilitates placement of an ICE catheter 102 as progressively illustrated in FIGS. 2A-2E As shown, in FIG. 2A, the delivery catheter 100 is inserted into the right atrium (RA) for example through the inferior vena cava via a femoral vein or the superior vena cava (not shown) through a jugular vein. As shown in FIG. 2B, inflation fluid is injected into the flow assist balloon 110 via inflation lumen 134 to inflate the flow assist balloon 110. The balloon 110 is inflated to take advantage of the blood flow through into and through the right atrium (RA) into the right ventricle (RV) and pulmonary artery (PA). In particular, inflation of the flow assist balloon 110 provides an expanded profile to interface with the blood flow from the right atrium (RA) into the right ventricle (RV) and pulmonary artery (PA) as illustrated by arrows 182. The interface with the blood flow provides an input force or momentum that assists movement or rotation of the delivery catheter 100 from the right atrium (RA) into the right ventricle (RV) and pulmonary artery (PA). In an illustrative embodiment, the balloon is inflated prior to insertion through the tricuspid valve and pulmonary valve to protect the valves from damage.

Figure 2D:
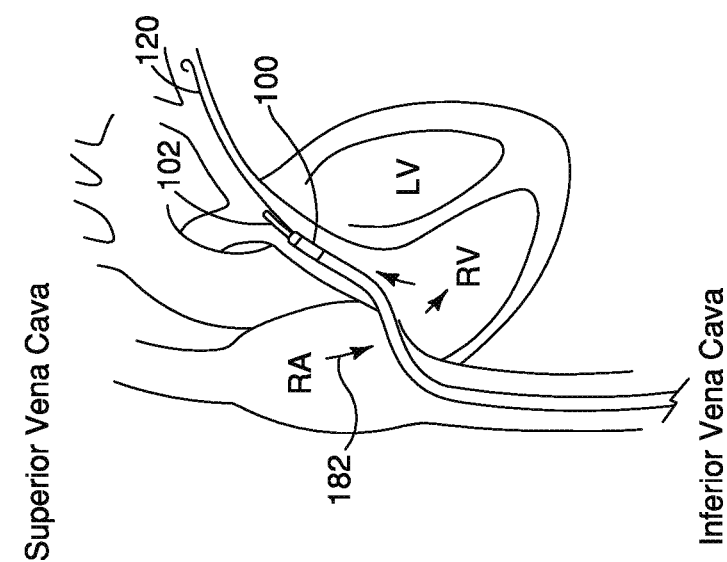

As shown in FIG. 2C, a guidewire 120 is inserted through the guidewire lumen 132 of the delivery catheter 100. The guidewire 120 has sufficient stiffness and rigidity to straighten out the curve from the right atrium (RA) to the pulmonary artery (PA) for preparation for insertion of the intracardiac imaging catheter 102 as shown in FIG. 2D. In particular, the guidewire 120 reduces an "S" curve configuration to provide a straighter path for placement of the ICE catheter 102. As shown in FIG. 2D, the intracardiac imaging catheter 102 is inserted through lumen 130 of the delivery catheter 100 for placement in the pulmonary artery (PA) for imaging. In illustrative embodiments, the guidewire 120 is inserted with the delivery catheter 100 or subsequent to intracardiac placement of the delivery catheter 100. In particular, the delivery catheter 100 can be inserted with the guidewire 120 for support.

As shown in FIG. 2E, once the imaging catheter 102 is in place, the delivery catheter 100 and guidewire 120 are withdrawn. In illustrative embodiments, the guide wire 120 is useful to re-advanced the delivery catheter 100 or other catheter into the pulmonary artery from the right ventricle (RV) or superior vena cava from the right atrium for treatment or imaging and is retained in the guidewire lumen 132. In alternate embodiments, the guidewire 120 is withdrawn as shown in FIG. 2E, but the delivery catheter 100 remains in place in the pulmonary artery (PA) during imaging or both the delivery catheter 100 and guidewire 120 remain in place.

In particular, in an illustrated embodiment, the imaging catheter 102 and transducer elements 166 are disposed in the delivery lumen 130 during imaging as described in illustrated embodiments herein. A transmission fluid is inserted into the delivery lumen through port 122 to provide a transmission medium for imaging. In alternate embodiments, the length of the delivery catheter 100 is sized so that the ICE or imaging catheter 102 extends outside the delivery catheter lumen 130 during imaging. In illustrative embodiments, the delivery catheter 100 remains in place to prevent prolapse of the ICE catheter 102 and facilitate torquability of the ICE catheter 102. The delivery catheter 100 can prevent prolapse of the imaging ICE catheter 102 from the (PA) into the (RV) and from the superior vena cava (SVC) into (RA).

Thus, as described, the delivery catheter 100 facilitates intracardiac placement of ICE catheter 102. In one embodiment, the ICE catheter 102 is positioned in the mid right atrium (RA) and the transducer array 166 or transducers are orientated toward the tricuspid valve to image the right ventricle, a portion of the right atrium and the tricuspid valve. In another embodiment, the ICE catheter 102 is orientated to provide an image of the aortic valve, coronary sinus and atrial septum for a transseptal procedure. The ICE catheter 102 can be placed in the right ventricle and orientated to image the left ventricle to screen for effusion or thrombus or mitral valve anatomy. Use of the delivery catheter 100 with the ICE catheter 102 enhances torquability of the ICE catheter 102 within the delivery catheter 100. The delivery catheter may also be positioned across the atrial septum into a pulmonary vein to support an ICE probe to examine the mitral valve or left atrial appendage.

FIGS. 3A-3B illustrate an alternate embodiment of an assembly of the present application including a flow assisted delivery catheter 100 for use in combination with an imaging or ICE catheter 102 where like numbers are used to refer to like parts in the previous FIGS. As shown in FIGS. 3A-3B, the shaft 104 includes a delivery lumen 130 sized for insertion of the ICE or imaging catheter 102 and guidewire 120 therethrough. For use, the guidewire 120 and ICE catheter 102 are inserted through connector 116 into the delivery lumen 130 for placement of the wire 120 and ICE catheter 102 for treatment as previously described and illustrated in FIGS. 2A-2E. The flow assist balloon 110 is inflated via fluid injected into the inflation lumen 134 via syringe 112 through inflation port 154 as described in the previous embodiment. In an alternate embodiment not shown, the delivery lumen 130 is sized to accommodate insertion of the ICE catheter 102 and guidewire 120 individually and the guidewire 120 is withdrawn prior to insertion of the ICE catheter 102 as described in illustrative embodiments.

FIGS. 4A-4B illustrate another embodiment of the delivery catheter 100 including a flow assist balloon 110 coupled to the distal end of the delivery catheter 100 and plurality of lumens along the body 104 as shown in FIG. 4B. The plurality of lumens include a delivery lumen 130 which is sized to accommodate the guidewire 120 and ICE catheter as shown in FIG. 4A and inflation lumen 134 to inflate the flow assist delivery balloon 110. The flow assist balloon 110 is inflated via inflation fluid injected into inflation lumen 134 through syringe 112A as shown in FIG. 4A. The delivery catheter 100 as shown in FIG. 4B also includes an inflation lumen 190 to inflate an inner balloon 192 disposed in the distal end of the delivery lumen 130 as shown in FIG. 4C. Inflation fluid is injected through the lumen 190 into the balloon 192 through inlet port 194.

The inner balloon 192 is inflated to retain the ICE catheter for use and provide an ultrasonic transmission fluid or medium through the inner balloon 192 as shown in FIG. 4C. In particular, the inner balloon 192 includes a proximal collar 196 coupled to the inner surface of the delivery lumen 130 aft of the inlet port 194 and a distal collar 198 coupled to the delivery lumen 130 forward of the inlet port 194. Inflation fluid is injected into lumen 190 via syringe 112B to inflate the inner balloon 192 to engage the ICE catheter disposed in the delivery lumen 130 for use. In an alternate embodiment not shown, the embodiment shown in FIGS. 4A-4B with the inner balloon 192 includes a separate guidewire lumen 132.

FIGS. 5A-5F illustrate another embodiment of an assembly of the present application. As shown, the assembly includes a delivery catheter 100 having an elongate shaft 104 and elongate guidewire 120. The delivery catheter 100 includes a flow assist balloon 110 coupled to the distal end of the elongate shaft 104 for intracardiac placement as previously described. The elongate shaft 104 includes a plurality of lumens including a delivery lumen 130 for an ICE catheter, inflation lumen 134 for inflating the flow assist balloon 110 and an inner inflation lumen 190 to inflate an inner balloon 192. Fluid is supplied into the inflation lumen 134 via syringe 112A and into inflation lumen 190 through syringe 112B.

Figure 5A:
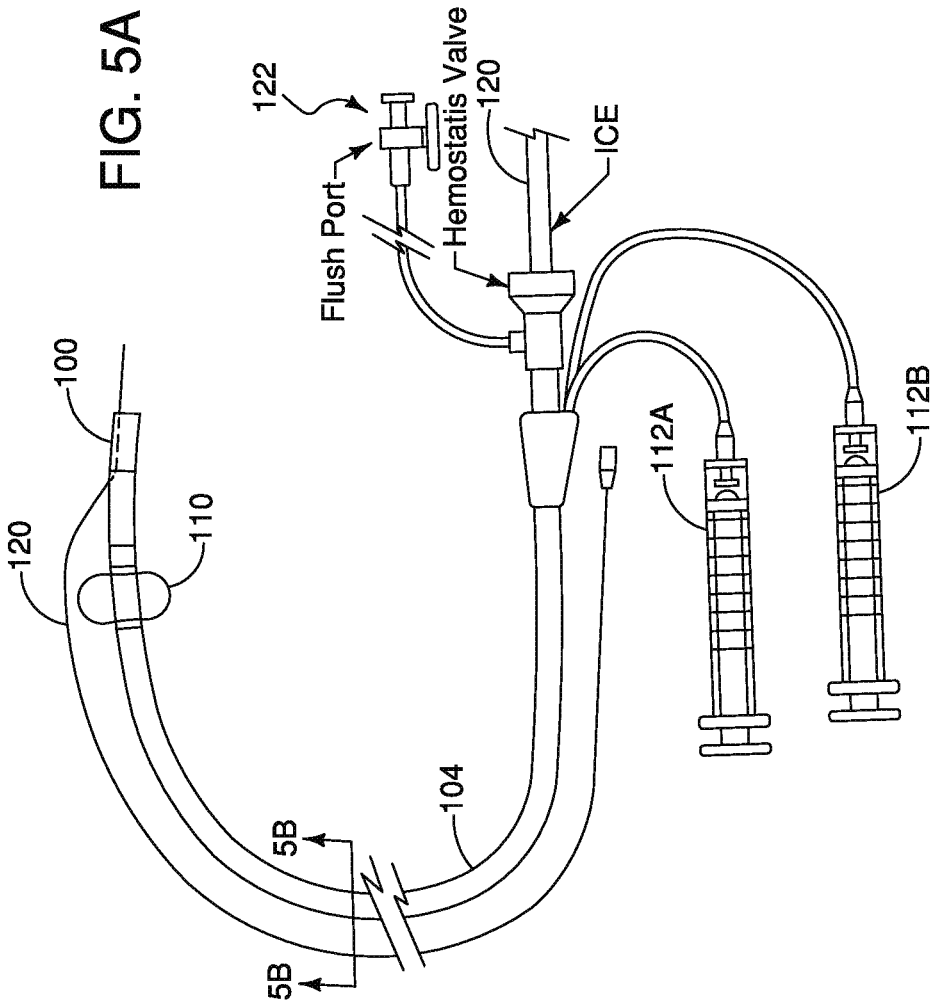
FIG. 5A illustrates another embodiment of the assembly of the present application.
Figure 5B:
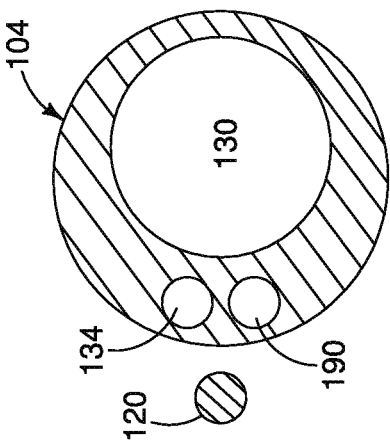
FIG. 5B is a cross-sectional view as taken along line 5B-5B of FIG. 5A.

As shown in FIGS. 5A and 5C the delivery catheter includes a rapid exchange guidewire lumen 200 at the distal end of the delivery catheter 100 for the guidewire 120. In the illustrated embodiment, the rapid exchange guidewire lumen 200 is formed along a distal length of the delivery lumen 130. The rapid exchange guidewire lumen 200 includes a proximal opening 202 formed through the shaft 104 into the delivery lumen 130 and a distal opening 204 formed through an opened distal end of the delivery lumen 130. The distal end of the wire 120 extends through the distal opening 204 along the delivery lumen 130 (guidewire lumen 200) and through the proximal opening 202 to track the delivery catheter 100 to the treatment site as shown in FIGS. 5C-5D.

As shown in FIG. 5E, the delivery catheter 100 also includes inner balloon 192 along the delivery lumen 130. The inner balloon 192 is inflated to engage the ICE catheter 102 inserted through delivery lumen 130 as shown in FIG. 5E. Fluid is injected into the inner balloon 192 through the inner inflation lumen 190 to inflate the inner balloon 192 via syringe 112B to abut the ICE catheter 102. As shown the inner balloon 192 includes proximal collar 196 coupled to inner surface of the delivery lumen 130 aft of the inlet port 194 and distal collar 196 coupled to an inner surface of the delivery lumen 130 spaced forward of the inlet 194. The inflated inner balloon 192 stabilizes the ICE catheter 102 and provides a transmission fluid surrounding the ICE catheter and in particular, the transducer elements 166 of the ICE catheter.

While in the illustrated embodiments, the rapid exchange or shortened guidewire lumen 200 is formed along a distal length of the delivery lumen 130, application is not limited to the illustrated embodiment and the rapid exchange guidewire lumen 200 can be formed of a separate shorted guidewire lumen at the distal end of the delivery catheter 100. Further the delivery catheter 100 can include a plurality of openings 202 for the guide wire 120 spaced about the circumference of the delivery catheter 100. In an illustrative embodiment, opening 202 is spaced 1-3 centimeters from the distal tip or end 108 of the delivery catheter 100.

Figures 6A, 6B, 6C, 6D:
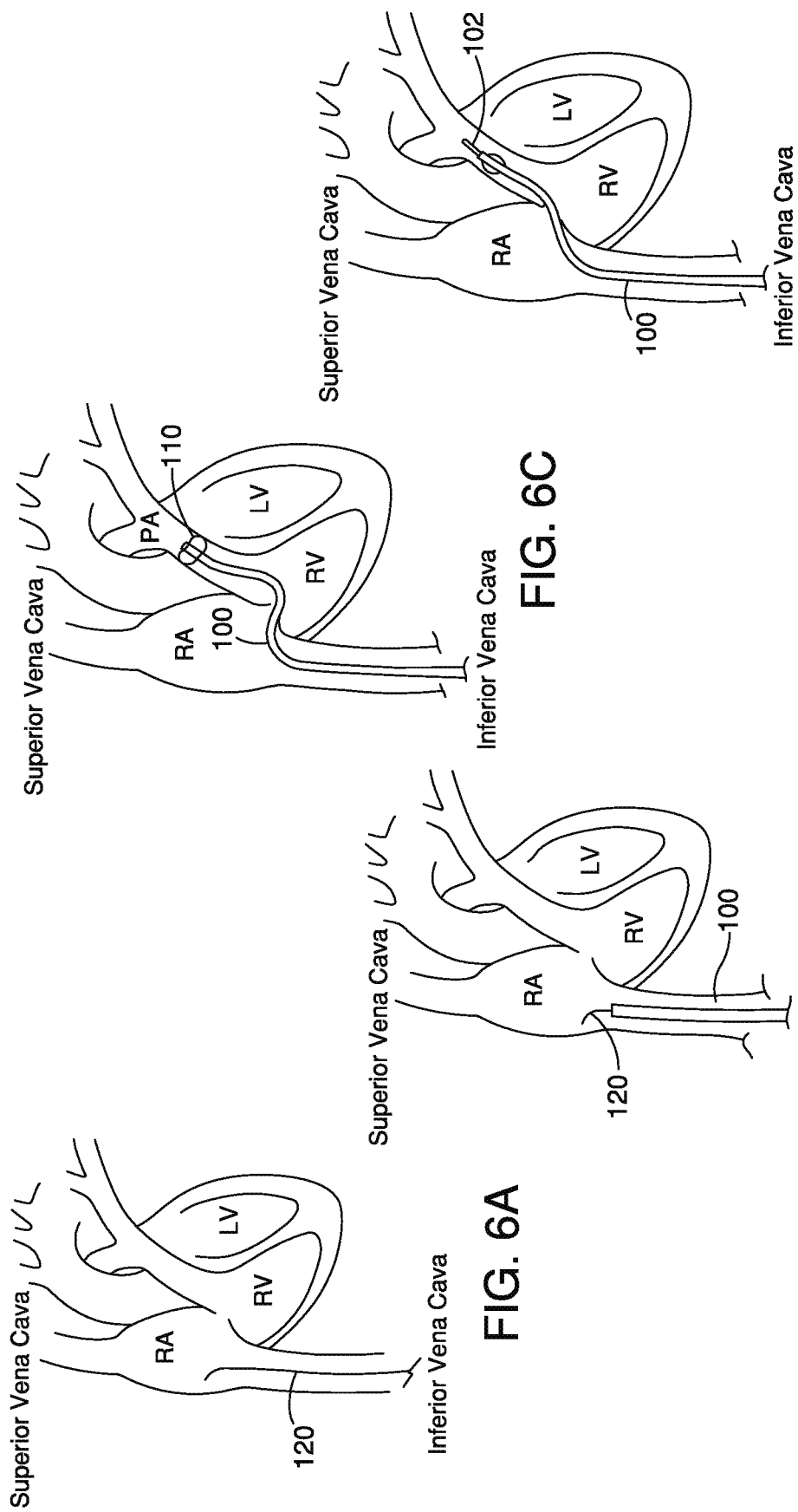
FIGS. 6A-6D progressively illustrate process steps illustrating use of the assembly of the present application.

FIGS. 6A-6D illustrate use of delivery catheter 100 having a rapid exchange or shortened guidewire lumen 200 as described. As shown, in FIG. 6A, in the illustrated embodiment, the guidewire 120 is percutaneously inserted into the patient and guided for intracardiac placement. In particular, in the illustrated embodiment, the guidewire 120 is advanced intravascularly into the right atrium to facilitate insertion of the delivery catheter 100. As shown, in FIG. 6B, the delivery catheter 100 is advanced along the guidewire 120 for intracardiac placement. As shown in FIG. 6C, inflation fluid is injected through syringe 112A to inflate balloon 110 to provide flow assistance or force to track the delivery catheter 100 into the right ventricle and the pulmonary artery to a treatment or imaging site. In particular, the balloon 110 is inflated to use blood flow to track the delivery catheter 100 into the right atrium, right ventricle and pulmonary artery.

In FIG. 6D when the delivery catheter 100 is in place, the balloon 110 is deflated and the ICE catheter 102 is inserted. In illustrative embodiments, the balloon 110 is deflated and the guidewire 120 is withdrawn prior to placement of the ICE catheter 102 or in illustrated embodiments the guidewire is withdrawn prior to inflation of the flow assist balloon 110. In other embodiments, the guidewire remains in place for insertion of the imaging catheter 102 and during imaging. As previously described, the delivery catheter 100 can be withdrawn or remain in place during imaging.

Figure 6E:
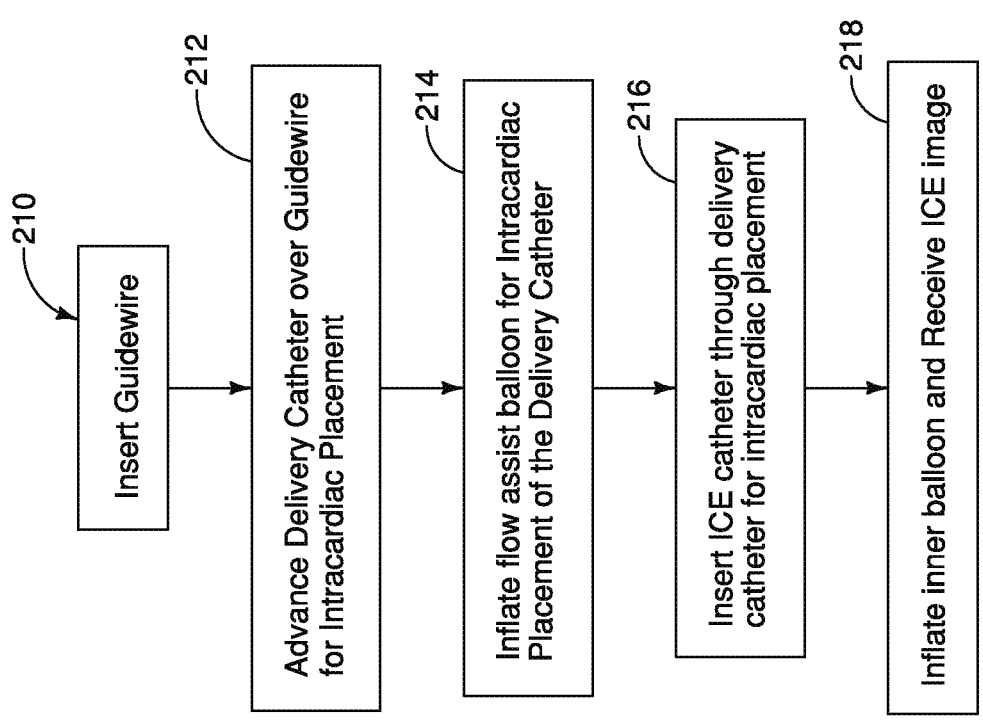
FIG. 6E is a flow chart illustrating steps for cardiac imaging using a delivery catheter of the present application.

FIG. 6E illustrates steps of the illustrated assemblies of the present application. As shown in step 210, a guidewire 120 is inserted and tracked intravascularly for intracardiac placement, for example to insert the delivery catheter 100 into the right atrium. In step 212, the delivery catheter 100 is inserted for intracardiac placement using the guidewire 120. In step 214 the flow assist balloon 110 on the delivery catheter 110 is inflated to assist placement of the delivery catheter 100 at the intracardiac treatment site, for example into the right atrium, right ventricle or pulmonary artery. In step 216 the ICE or imaging catheter 102 is advanced through the delivery lumen 130 to an imaging or treatment site for example, in the pulmonary artery. In an example embodiment, the flow assist balloon 110 is deflated prior to insertion of the ICE catheter 102. The inner balloon 190 is inflated in step 218 to abut the ICE catheter 102 and provide a fluid bladder for transmission of ultrasonic imaging waves during use. Alternatively, fluid is injected into the delivery lumen for imaging. In illustrative embodiments, the guidewire is withdrawn prior to insertion of the ICE catheter or in an alternate embodiment the guidewire 120 is withdrawn prior to inflation of the flow assist balloon. In illustrative embodiments, the delivery catheter 100 includes a separate guidewire lumen 132, 200 and the guidewire 120 remains in place to reposition the delivery catheter 100 for use.

In an alternate embodiment of a delivery catheter 100 having an inner balloon 192 and outer balloon 110, the delivery catheter 100 includes delivery lumen 130, inflation lumen 134, inflation lumen 190 and a guide wire lumen 120 that extends along the length of the delivery catheter between the proximal and distal ends.

FIG. 7A illustrates another embodiment of an intracardiac echocardiography delivery catheter 100A having an elongate cylindrical shaped body or shaft 104A where like numbers are used to identify like parts in the previous FIGS. As shown, the elongate body or shaft 104A includes a relatively stiff proximal length 220 and a relatively or ultra-flexible distal length 222. The relatively stiff proximal length 220 provides pushability and torquability for insertion and the relatively flexible length 222 provides sufficient flexibility or bendability for intracardiac navigation, for example, through the inferior vena cava into the right atrium, right ventricle and into the pulmonary artery for placement of an imaging or ICE catheter 102. As previously described, placement of the delivery catheter 100A is assisted by a flow assist balloon 110A at the distal end of the catheter shaft 104A (or ultra-flexible distal length 222).

In the illustrated embodiment, the balloon 110A is an asymmetrical balloon as shown in FIG. 7B to enhance navigation and placement of the catheter 100A as will be described herein. Balloon 110A is inflated via syringe 112 to assist placement of the delivery catheter 100A as previously described. In an illustrative embodiment, a length dimension of the relatively stiff proximal length 220 of the catheter is approximately 30-50 cm (11-20 inches) and a length dimensions of the flexible distal length 222 of the catheter is approximately, 30 cm (11 inches).

In the illustrated embodiment shown in FIG. 7A, the catheter shaft 104A of the delivery catheter 100A is a multiple lumen shaft 104A as shown in FIGS. 7C-7G. As shown, the multiple lumen shaft 104A includes an ICE delivery lumen 130, guidewire lumen 132, and a balloon inflation lumen 134 formed along the proximal and distal lengths 220, 222 of the shaft 104A. In the embodiment shown, the multiple lumens are formed along an inner core or lumen structure formed of a plurality of microtubes 230 for each of the plurality of lumens. In illustrated embodiments, the plurality of microtubes 230 are formed of polytetraflouroethylene (PTFE), such as PTFE sold under the trademark Teflon® by Chemours Company FC of Delaware. The Teflon® microtubes 230 provide a lubricous inner surface for use and for slideable placement and movement of the ICE catheter 102 and guide wire 120.

The stiff proximal length 220 is formed of a stiff perimeter or wall structure 232 formed about the core or lumen structure. In illustrated embodiments, the stiff perimeter structure 232 of the proximal length 220 is formed of hard durometer polymer material such as a polyether block amide, for example, Pebax® available from Arkema France Corporation of Colombes France having a hardness range of 63 Shore D, or polyvinyl alcohol (PVAl) urethane material or similar material having a hardness range between 25-72 Shore D to form the relatively stiff proximal length 220 of the catheter shaft 104A.

The flexible distal length 222 of the catheter shaft 104A has a relatively flexible perimeter or wall structure 234 formed of helical coil 240 embedded within a soft polymer body or layers 242 (inner and outer layers). The helical coil 240 is formed of an aluminum, stainless steel or other material. In an illustrated embodiment the helical coil 240 provides a relatively high hoop strength to provide structural integrity for the multiple lumens of the catheter shaft 104A and the polymer body or layers 242 and embedded helical coil 240 provide a flexible and bendable distal length for intracardiac placement of the catheter 100A. Illustratively, flexible polymer body or layers 242 are formed of a low durometer or hardness material to provide the flexibility for the distal length 222. Illustrative low durometer materials include polychloroprene layer(s) or material having a hardness of approximately 60 Shore A or other material having similar durometer or hardness.

As shown in FIG. 7C the catheter shaft 104A includes a transition structure connecting the proximal and distal lengths 220, 222 to form the elongate length of the catheter shaft 104A. As shown, the transition structure includes a tubular braid 252 having a length that extends along a transition zone between the proximal and distal lengths 220, 222 to connect the proximal and distal lengths of the catheter shaft 104A. The tubular braid 252 encloses the core or lumen structure as shown FIGS. 7C and 7F and is formed of a Nitinol-nickel-titanium alloy, stainless steel or fabric material. As shown, the relatively stiff perimeter structure 232 of the proximal length 220 and flexible perimeter or wall structure 234 of the distal length 222 are formed along the proximal and distal ends of the transition zone, respectively. In addition to the structure shown, in illustrated embodiments, the catheter shaft 104A includes on or more stiffening wires formed along the structure of the catheter shaft 104A for steerability.

Figure 7H:
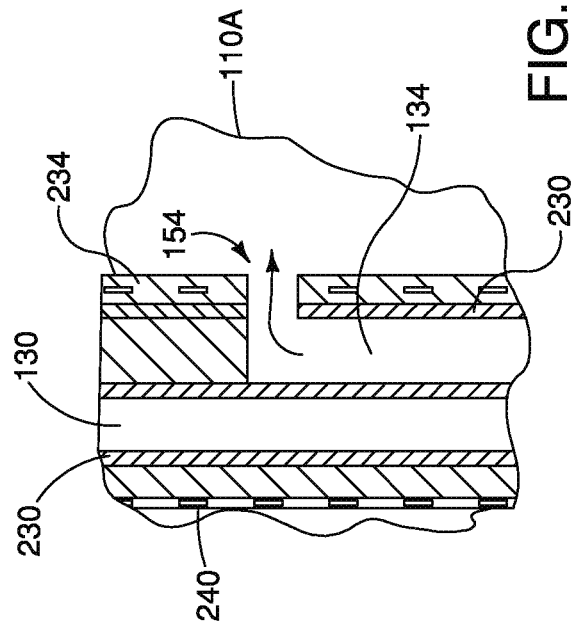
FIG. 7H is a detailed view of a distal portion of a shaft of the intracardiac delivery catheter of an illustrative embodiment.
Figure 7G:
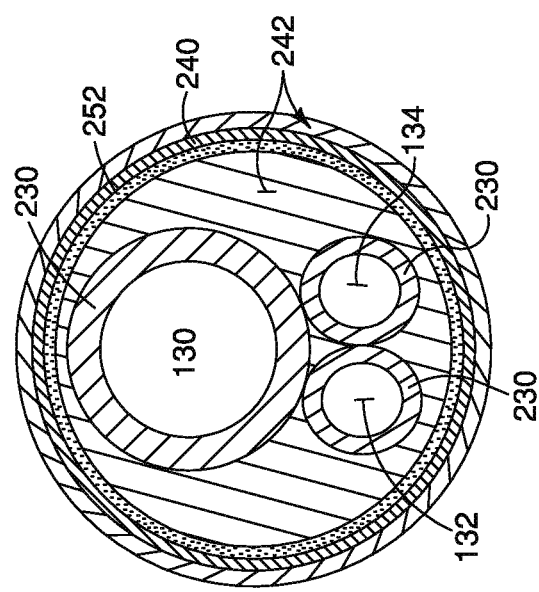
FIG. 7G is a cross-sectional view taken along line G-G of FIG. 7C.
Figure 7K:
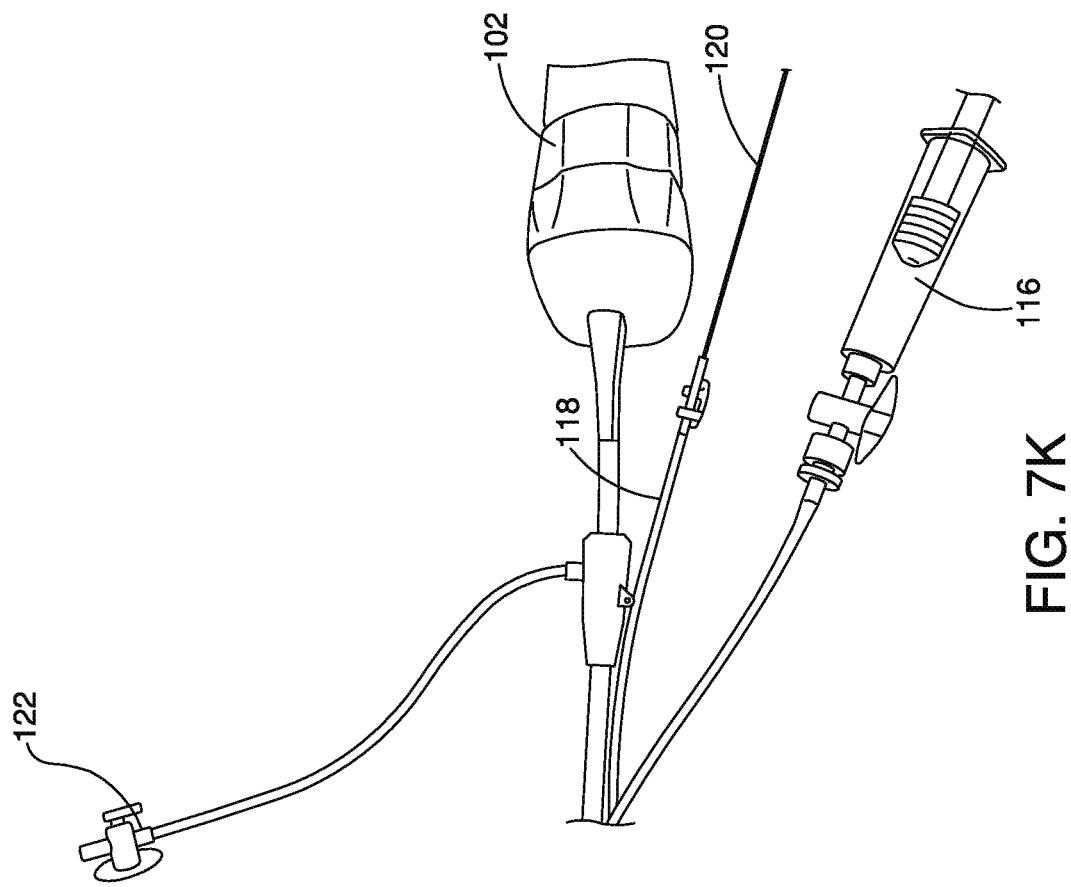
FIG. 7K illustrates a proximal end of the intracardiac delivery catheter and assembly.
Figure 7I:
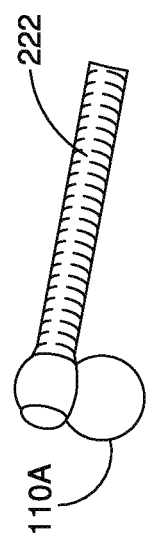
FIG. 7I illustrates an embodiment of an asymmetrical balloon at a distal end of the catheter shaft of the intracardiac delivery catheter.
Figure 7J:
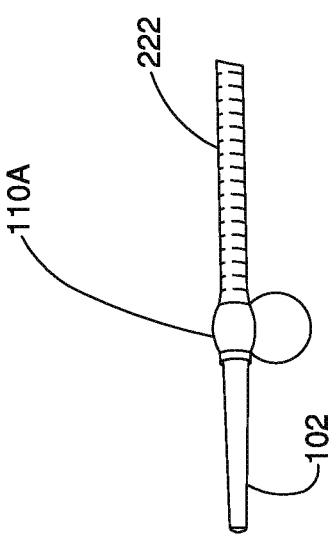
FIG. 7J schematically illustrates a distal end of the catheter shaft of the embodiment shown in FIGS. 7A-7I with an intracardiac imaging catheter (ICE) extending through a distal opening of the catheter shaft.

In the illustrated embodiment shown, the core or lumen structure is formed of a plurality of microtubes 230 that extend along the length of the catheter shaft 104A, however, in alternate embodiments, the microtubes 230 extend along the proximal length of the catheter shaft and the lumens along the distal length are formed or molded along the distal perimeter structure 234 or shaft 104A. As previously described, and as shown in FIG. 7H, the length of the inflation lumen 134 extends from the proximal end of the catheter shaft 104A to a distal port 154 opened to an interior of the balloon 110A to inflate the balloon 110A at the distal end 108 of the catheter shaft 104A as shown in FIGS. 7I-7J. The guide wire lumen 132 and ICE delivery lumen 130 extend the length of the catheter shaft 104A from the proximal end 106 to distal openings at the end of the catheter shaft 104A. FIG. 7K illustrates the syringe 112 (with control valve), ICE catheter 102 and guide wire connector 118 or port at the proximal end of the catheter shaft 104A.

Figure 8B:
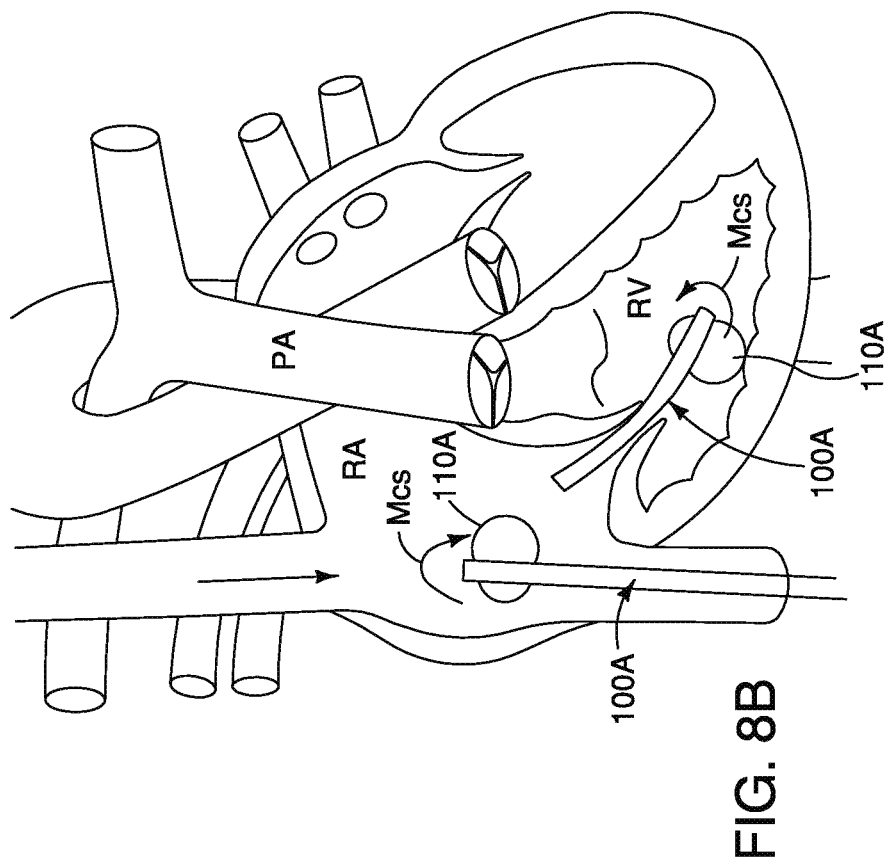
FIG. 8B schematically illustrates an embodiment for intracardiac navigation of an asymmetric balloon.
Figure 8A:
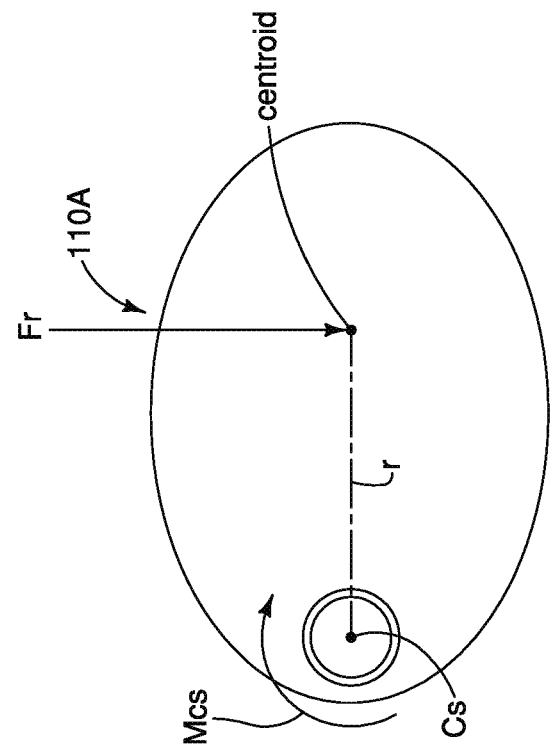
FIG. 8A schematically illustrates force(s) and moment interacting with an asymmetric balloon.
Figure 9D:
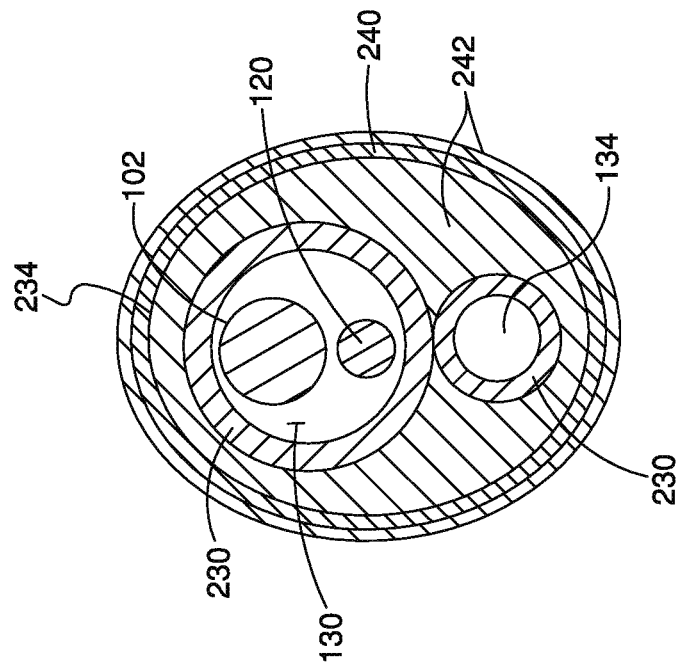
FIG. 9D is a cross-sectional view taken along line D-D of FIG. 9A.
Figure 9C:
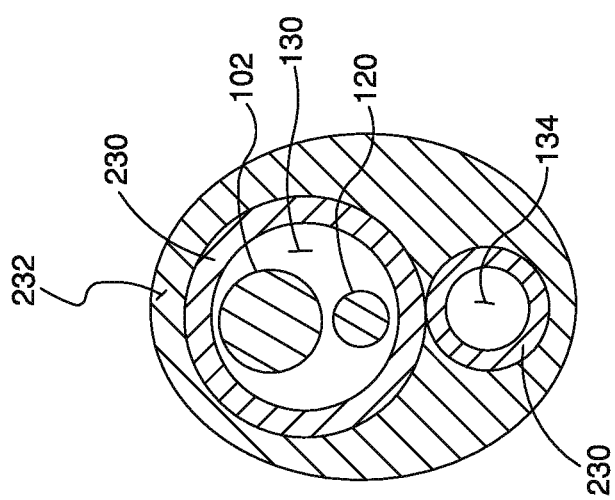
FIG. 9C is a cross-sectional view taken along line C-C of FIG. 9A.

As previously described and shown in FIG. 7B, in an illustrative embodiment, the balloon 110A is an asymmetric balloon where centroid c of the body of the balloon 110A is off-set from a longitudinal axis of the catheter shaft $C_s$ as shown in FIG. 8A. During use as schematically shown in FIG. 8A, blood flow or cardiac pressure provides a distributed force along a surface of the balloon 110A. In contrast to a symmetrical balloon, force applied to the asymmetrical balloon 110A imparts a resultant force $F_r$ through a centroid c of the balloon spaced from the longitudinal axis of the catheter shaft $C_s$ to define a moment arm r or asymmetric portion between the catheter shaft $C_s$ and centroid c. The resultant force $F_r$ and moment arm r imparts a moment $M_{CS}$ relative to the catheter shaft $C_s$ having a magnitude provided by $M_{CS}=F_r*r$. Thus, as described, the asymmetric portion of the balloon 100A is orientated to assist with steering and placement of the delivery catheter 100 for use. For example, the asymmetric portion is oriented to steer the catheter 100 through the tricuspid valve into the right ventricle and through the pulmonary valve into the pulmonary artery.

As shown in FIG. 8B during use and insertion, the balloon is orientated to impart a clockwise moment $M_{CS}$ to align a tip of the delivery catheter 100A with the tricuspid valve for insertion into the (RV) and as shown in FIG. 8B, the balloon 110A is orientated to impart a counterclockwise moment $M_{CS}$ relative to the catheter shaft 104A to align the tip of the delivery catheter 100A with the pulmonary artery (PA) for access to an imaging or treatment site. Additionally, the off-axis alignment of the balloon reduces the surface area to reduce back pressure and force imparted to the catheter 100A during insertion.

While illustrative embodiments show application of the asymmetric balloon for placement of the delivery catheter 100A, application of the asymmetric balloon 110A as described is not limited to delivery catheter 100A and can be used for navigation of other intracardiac or delivery catheters into the body or to a treatment site. In an illustrative embodiment, the asymmetric balloon 110A is formed of an elongate generally tubular shaped body having spaced first and second ends connected to an outer surface of the flexible perimeter or wall structure 234 or catheter shaft 104A. The asymmetric shape is formed via a thinner or stressed wall thickness of the tubular shaped body so that inflation of the interior cavity of the balloon forms the asymmetric shape of the balloon 110A.

FIGS. 9A-9D illustrate an alternate embodiment of the delivery catheter 100A having a stiff proximal length 220 and are relatively flexible distal length 222 as previously described with respect to FIGS. 7A-7G. In the embodiment shown, the multiple lumen catheter shaft 104A includes ICE delivery lumen 130 and balloon inflation lumen 134. Similar to the embodiment illustrated in FIGS. 3A-3B, the delivery lumen 130 is sized to accommodate the ICE imaging catheter 102 and guidewire 120 for placement of the delivery catheter 100A for use.

FIGS. 10A-10E illustrate another embodiment of a delivery catheter 100A including a stiff proximal length 220 and a flexible distal length 222 as previously described. In the illustrated embodiment shown, the shaft 104A includes an ICE delivery lumen 130 and an inflation lumen 134 along the proximal and distal lengths 220, 222. As shown in FIG. 10C, the distal length includes a shortened guidewire lumen 132 (200). The rapid exchange or shortened guidewire lumen 132 (200) includes a proximal opening 202A and a distal opening 204A (as shown in FIG. 10A) formed through an opened distal end of lumen 132 at the distal end of the catheter shaft 104A. The distal end of the wire 120 extends through the proximal opening 202A and the distal opening 204A to track the delivery catheter to the treatment site. The proximal opening 202A is spaced from the proximal end of the catheter shaft 104A. In the embodiment shown, the length of the rapid exchange or shortened guidewire lumen 132 (200) extends along the flexible distal length 222, however, application is not limited to the length of the rapid exchange guide wire lumen 132 shown and in illustrative embodiments the length can extend along the entire flexible distal length 222 or along the distal length and a portion of the stiff proximal length 220 so that the proximal opening 202A is located along the stiff proximal length 220.

Figure 11A:
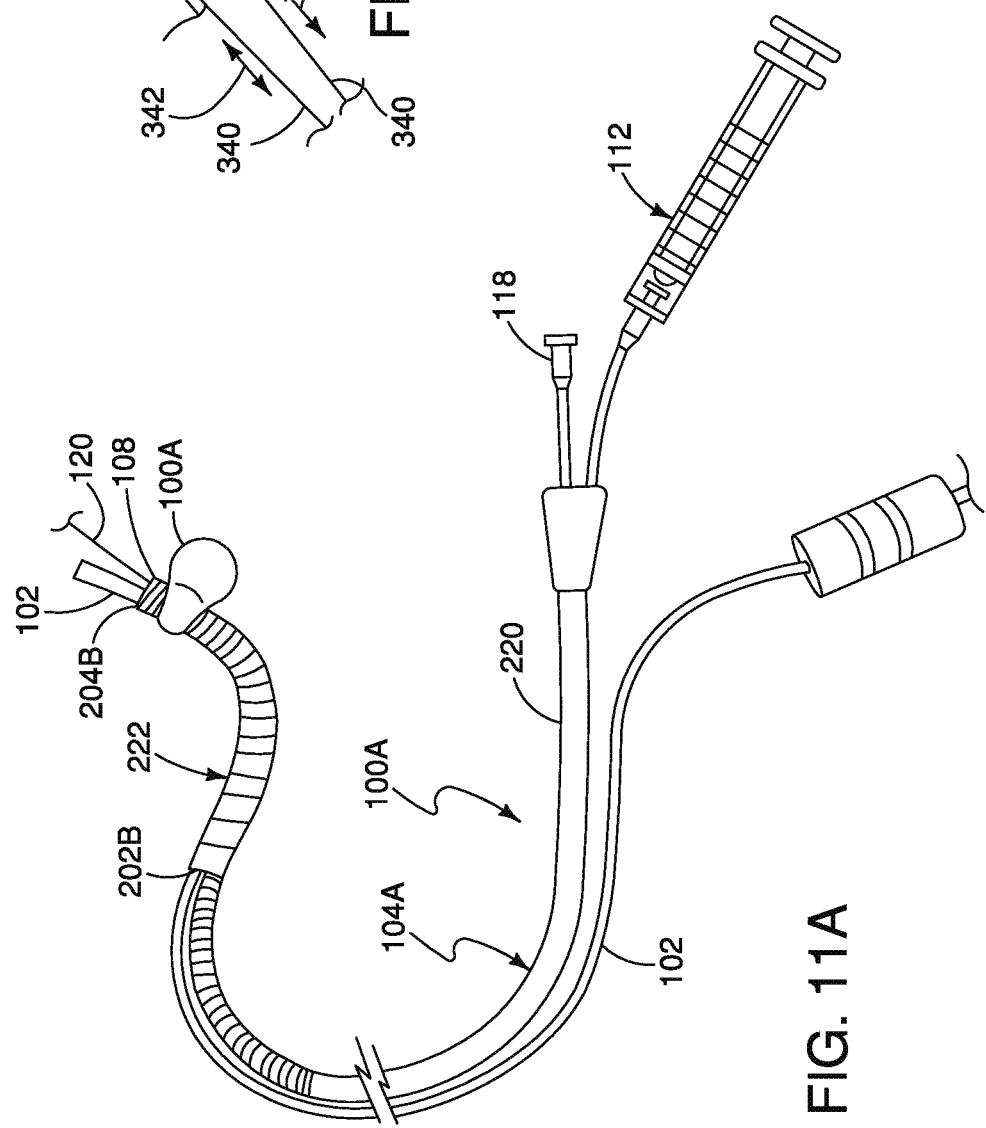
FIG. 11A illustrates another embodiment of an intracardiac delivery catheter having a shorted imaging catheter (ICE) lumen.

FIGS. 11A-11D illustrate another embodiment of a delivery catheter 100A including a stiff proximal length 220 and a flexible distal length 222 as previously described. In the illustrated embodiment, the catheter 100A includes a shortened ICE delivery lumen 130 along the relatively flexible distal length 222 of the catheter shaft as shown in FIG. 11B. As shown, the flexible distal length 222 includes ICE delivery lumen 130 having a proximal opening 202B spaced from the proximal end 106 of the catheter shaft 104A and a distal opening 204B (shown in FIG. 11A) at the distal end 108 of the catheter shaft 104A.

Thus, as shown, the ICE delivery lumen 130 is formed along the flexible distal length 222 of the catheter shaft. For use, the stiff proximal length 220 provides sufficient rigidity and pushability to insert the delivery catheter 100A and ICE catheter 102 through a patient's vascular to the right atrium. Guide wire 120 is inserted through lumen 132 and the balloon 110A is inflated to float the delivery catheter into right ventricle (RV) and pulmonary artery (PA) for imaging. In alternate embodiment, not shown, both the guide wire lumen 132 and ICE delivery lumen 130 have a shortened length extending along the flexible distal length 222 of the catheter shaft 104A. In an alternate embodiment not shown, the shortened ICE delivery lumen 130 extends along the flexible distal length 222 and a portion of the stiff proximal length 220 so that proximal opening 202B is disposed along the stiff proximal length 220 of the catheter shaft 104A.

Figure 12A:
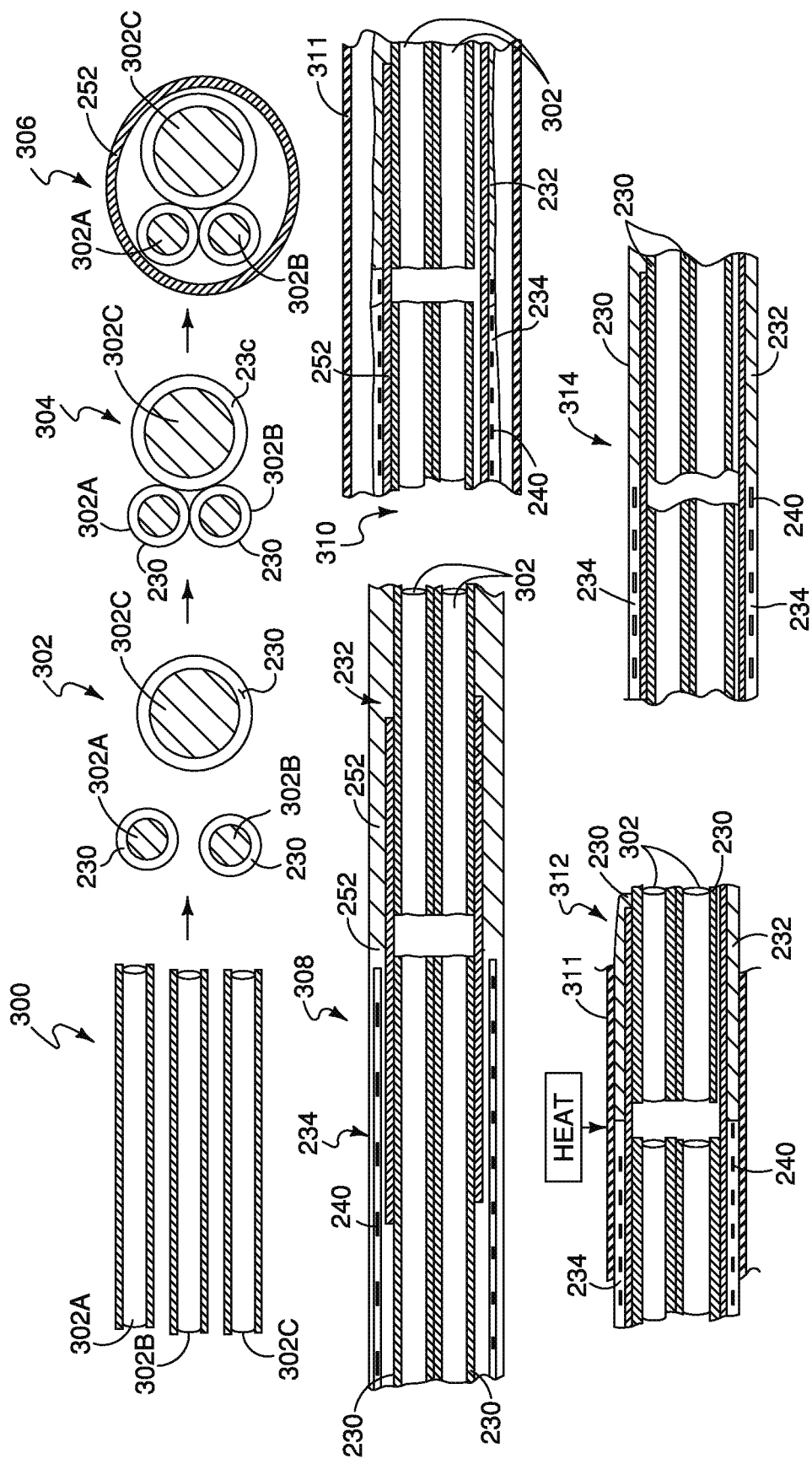
FIG. 12A illustrates fabrication steps for embodiments of the present application.

FIG. 12A schematically illustrates fabrication of a multiple lumen delivery catheter 100A having a stiff proximal length 220 and an ultra-flexible distal length 222 in accordance with illustrative embodiments described. As progressively shown in step 300, a plurality of mandrels 302A, 302B, 302C having different sized diameters to correspond to the different sized lumens are coated with a Teflon® coating or other lubricous material. In step 302, microtubes 230 are assembled on the mandrels 302A-302C to form the plurality of lumens. As previously discussed, in illustrated embodiments, the microtubes 230 are formed of a Teflon material to provide a lubricous inner surface of the lumens. In step 304, the microtubes 230 are joined along a length thereof to form a multiple lumen or core structure. Illustratively, the microtubes 230 are connected via an adhesive or other material. An outer surface of the tubular liners can be roughened to enhance the adhesive connection of the microtubes 230.

As shown in step 306, a tubular braid 252 is deposited over an outer circumference of the microtubes to form the transition between the proximal and distal lengths 220, 222 of the catheter shaft. In step 308, an outer surface of the core or lumen structure is coated with the hard polymer material along proximal length and tubular braid 252 along a transition length and the soft polymer material or layers 242 and helical coil 240 are deposited over a distal length of the core or lumen structure and a transition length of the tubular braid 252 to form the proximal and distal lengths 220, 222 of the catheter shaft 104A. As shown in step 310, a heat shrink tube 311 is placed about the length of the structure and in step 312, heat is supplied to shrink tube 311 to impart pressure to the polymer coatings or layers. In an illustrated embodiment the heat shrink tube is a fluorinated ethylene propylene (FEP) heat shrink tube. Heat and pressure imparted by the shrinking diameter of the shrink tube 311 causes the polymer coatings or layers to flow into the interspaces of the tubular braid 252 to connect the relatively stiff proximal length 220 of the catheter and the relatively flexible distal length 222 of the catheter and coil. Thereafter, in step 314 the heat shrink tube 311 and mandrels 302 are removed for assembly of the proximal hub and balloon to the catheter shaft 104 to form the delivery catheter 100A.

In alternate embodiments, the length of the microtubes 230 extends along the proximal length 220 and not along the distal length 222 and the polymer coating or layers form the lumen structure for the multiple lumens along the distal length 222. In alternate embodiments as disclosed shortened microtubes 230 are used to form a shortened distal guide wire lumen 132 or ICE delivery lumen 130.

Figure 12B:
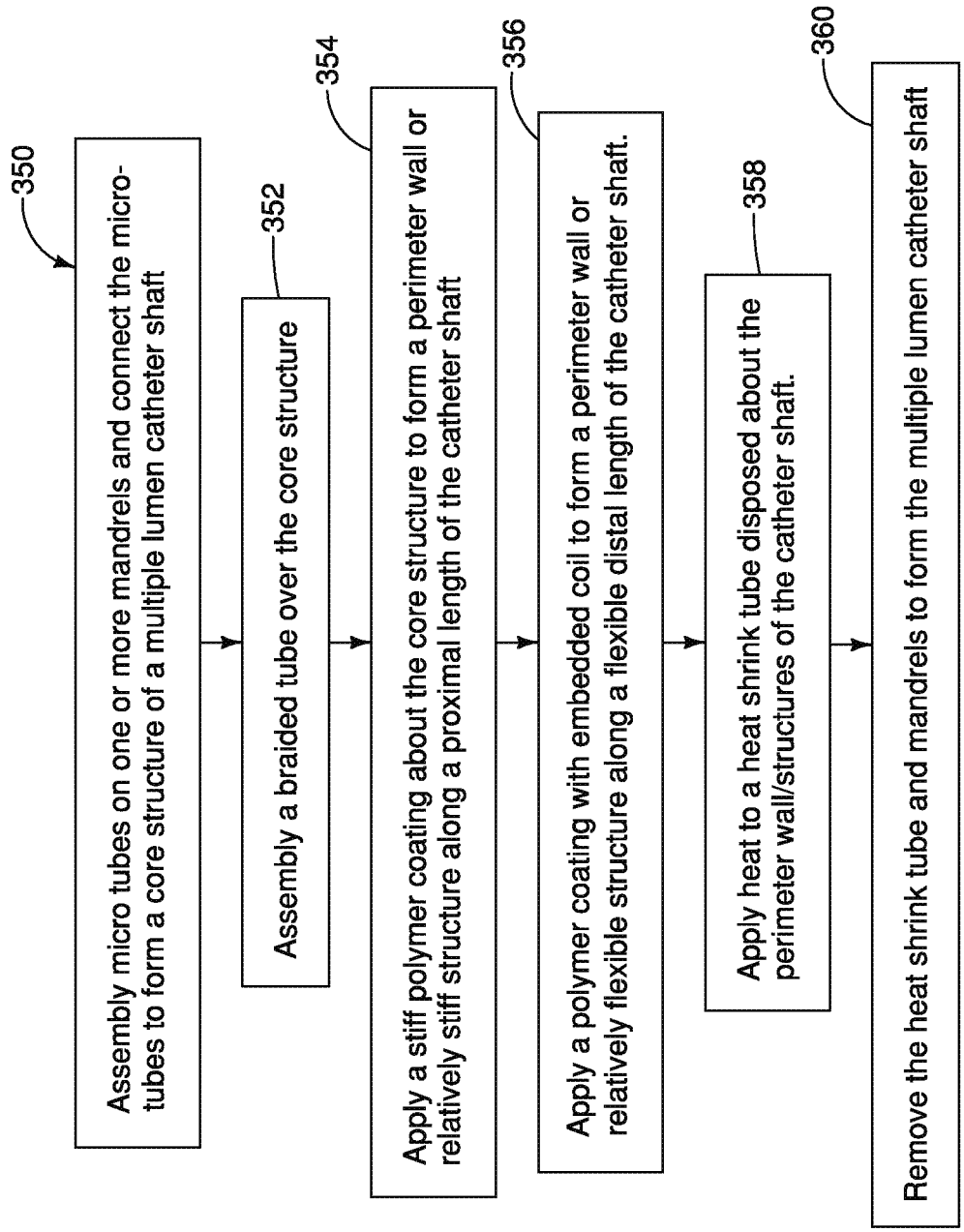
FIG. 12B is a flow chart illustrating a fabrication embodiment of a multiple lumen intracardiac delivery catheter of the present application.

FIG. 12B is a flow chart illustrating process steps for fabrication of the delivery catheter 100A and shaft according to embodiments of the present application. As previously described a plurality of mandrels 302 are used to form a plurality of lumens of a multiple lumen catheter shaft. As shown in step 350 a plurality of microtubes 230 are assembled over mandrels and adhesively connected to form the multiple lumen/core structure. In step 352, tubular braid 252 is assembled over the lumen or core structure to form a transition zone. In step 354 a proximal length of the structure is coated with a hard durometer polymer material to form the stiff proximal length 220 of the catheter. In step 356, a helical spring is assembled over the distal length between inner and outer low durometer polymer layers to form the flexible distal length 222. In step 358 heat is applied to a heat shrink tube 311 to provide heat and pressure about an outer circumference of the coatings or layers to provide material flow to form the perimeter wall structures of the proximal and distal lengths 220, 222 of the catheter shaft connected along a transition length through the braided tube 252. In step 360 the heat shrink tube 311 and mandrels 302 are removed.

Figure 13:
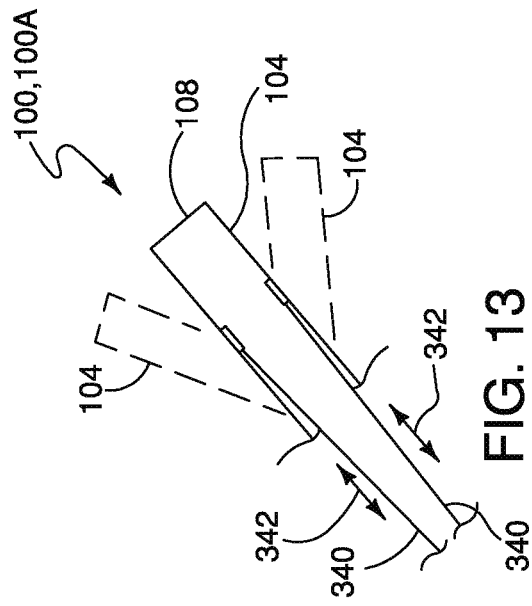
FIG. 13 schematically illustrates an embodiment of a steerable distal tip for embodiments of the delivery catheter of the present application.

FIG. 13 illustrates a distal tip of an illustrative embodiments of the delivery catheter 100, 100A. As shown, elongate control wires 340 are coupled to the distal tip of the delivery catheter 100, 100A to adjust an angle (as shown in phantom) of the distal tip of the delivery catheter relative to the longitudinal length of the shaft 104, 104A. As schematically shown, the length of the control wire 340 extends from the distal tip to the proximal end of the catheter shaft 104 or hub so that the user can intravenously adjust the angle of the distal tip to steer the delivery catheter 100, 100A to the treatment or imaging site via movement of the control wire(s) 340 as illustrated by arrows 342. In illustrated embodiments, one or more control wires 340 extend along one or more control wire lumens (not shown) formed along the catheter shaft 104 and illustrative embodiments include one or more control wires 340 and one or more control wire lumens (not shown).

While illustrative embodiments are shown, application of the present invention is not limited to the illustrated embodiments and changes and modifications can be made as will be appreciated by those skilled in the art. For example, the flow assisted delivery catheter 100 can be used for placement of an ICE or imaging catheter 102 at alternate imaging sites. Further application of the present invention is not limited to the particular order of steps described. As described, application of the illustrative embodiments allow for placement of an imaging catheter at an intracardiac imaging site without damage to the superior vena cava or placement in a pulmonary artery or other intracardiac treatment site without damage to tricuspid or pulmonary valves via a balloon tipped delivery catheter 100. While specific combination of elements are shown in illustrated embodiments, it should be appreciated that features and elements of the illustrated embodiments can be combined to form alternate embodiments of the invention.

What is claimed is:

1. A method for providing an echocardiographic image comprising steps of:
   intravascularly inserting an intracardiac delivery catheter including an asymmetric shape flow assist balloon at a distal end of the delivery catheter for placement of an imaging catheter including one or more transducer elements;
   inflating the asymmetric shape flow assist balloon at the distal end of the delivery catheter;
   using the inflated flow assist balloon to advance the intracardiac delivery catheter;
   orientating an asymmetric portion of the asymmetric shape flow assist balloon in a first orientation to form a moment arm to impart rotation to the delivery catheter to align a tip of the delivery catheter with a right ventricle and advancing the delivery catheter through a tricuspid valve into the right ventricle;
   orientating the asymmetric portion of the asymmetric shape flow assist balloon in a second orientation different from the first orientation to align the moment arm to impart rotation to the delivery catheter to align the tip of the delivery catheter with a pulmonary artery and advancing the delivery catheter through a pulmonary valve into the pulmonary artery;
   inserting the imaging catheter into a deliver lumen of the delivery catheter;
   slideably advancing the imaging catheter through the delivery lumen of the delivery catheter to position the imaging catheter at an intracardiac treatment site in the pulmonary artery; and
   receiving image feedback from the one or more transducer elements of the imaging catheter.

2. The method of claim 1 wherein the steps of orientating the asymmetric portion of the flow assist balloon include:
   rotating a shaft of the delivery catheter to a first position to locate the flow assist balloon in the first orientation; and
   rotating the shaft of the delivery catheter to a second position to locate the flow assist balloon in the second orientation.

3. A method for providing an echocardiographic image comprising the steps of:
   intravascularly inserting an intracardiac delivery catheter including an asymmetric shape flow assist balloon at a distal end of the delivery catheter for placement of an imaging catheter including one or more transducer elements;
   inflating the asymmetric shape flow assist balloon at the distal end of the delivery catheter;
   using the inflated flow assist balloon to advance the intracardiac delivery catheter;
   orientating an asymmetric portion of the asymmetric shape flow assist balloon to form a moment arm to impart rotation to a tip of the delivery catheter to align the tip of the delivery catheter with a pulmonary artery;
   advancing the delivery catheter through a pulmonary valve into the pulmonary artery;
   inserting the imaging catheter into a delivery lumen of the delivery catheter;
   slideably advancing the imaging catheter through the delivery lumen of the delivery catheter to position the imaging catheter at an intracardiac treatment site in the pulmonary artery; and
   receiving image feedback from the one or more transducer elements of the imaging catheter.

4. The method of claim 3 wherein the step of orientating the asymmetric portion of the flow assist balloon comprises:
   rotating a shaft of the delivery catheter to align the tip of the delivery catheter for insertion into the pulmonary artery.

* * * * *